(12) United States Patent
Hayakawa et al.

(10) Patent No.: US 11,833,316 B2
(45) Date of Patent: Dec. 5, 2023

(54) GUIDE WIRE, MEDICAL DEVICE, AND TREATMENT METHOD

(71) Applicant: TERUMO KABUSHIKI KAISHA, Tokyo (JP)

(72) Inventors: Koichi Hayakawa, Machida (JP); Kazunari Fukami, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 988 days.

(21) Appl. No.: 16/584,993

(22) Filed: Sep. 27, 2019

(65) Prior Publication Data
US 2020/0023168 A1    Jan. 23, 2020

Related U.S. Application Data

(63) Continuation of application No. PCT/JP2018/012850, filed on Mar. 28, 2018.

(30) Foreign Application Priority Data

Mar. 31, 2017 (JP) ................................ 2017-071873

(51) Int. Cl.
*A61M 25/09* (2006.01)
*A61B 17/00* (2006.01)
(Continued)

(52) U.S. Cl.
CPC ... *A61M 25/09041* (2013.01); *A61B 17/0057* (2013.01); *A61B 17/3468* (2013.01);
(Continued)

(58) Field of Classification Search
CPC ...... A61B 17/3496; A61B 2017/22044; A61B 2025/09083; A61B 2025/09133
See application file for complete search history.

(56) References Cited

U.S. PATENT DOCUMENTS 5,242,418 A    9/1993  Weinstein
5,478,313 A   12/1995  White
(Continued)

FOREIGN PATENT DOCUMENTS

CN        102370513 A     3/2012
DE   10 2011 107 614 A1   1/2013
(Continued)

OTHER PUBLICATIONS

International Search Report (with English translation) and Written Opinion issued in corresponding International Patent Application No. PCT/JP2018/012850, 8 pages (dated Jul. 3, 2018).
(Continued)

*Primary Examiner* — Alexander J Orkin
(74) *Attorney, Agent, or Firm* — BUCHANAN INGERSOLL & ROONEY PC

(57) ABSTRACT

A guide wire, a medical device, and a medical method are able to achieve satisfactory workability and while ensuring safety by preventing a puncture needle portion from performing erroneous puncture. A guide wire for guiding a dilator to be inserted into a living body includes a shaft portion, a puncture portion fixed to a distal portion of the shaft portion, and whose distal side includes a needle portion for forming a hole in a biological tissue, and a deformable deformation portion fixed to the shaft portion or the puncture portion. The deformation portion located inside the dilator restricts deflection of the distal portion of the shaft portion.

18 Claims, 24 Drawing Sheets

(51) Int. Cl.
   *A61B 17/34* (2006.01)
   *A61B 18/14* (2006.01)
   *A61B 17/22* (2006.01)

(52) U.S. Cl.
   CPC ...... *A61B 17/3496* (2013.01); *A61B 17/3403* (2013.01); *A61B 18/1477* (2013.01); *A61B 2017/00022* (2013.01); *A61B 2017/00243* (2013.01); *A61B 2017/00575* (2013.01); *A61B 2017/22044* (2013.01); *A61M 2025/09083* (2013.01); *A61M 2025/09133* (2013.01)

(56) References Cited

U.S. PATENT DOCUMENTS

| | | | |
|---|---|---|---|
| 5,645,556 | A | 7/1997 | Yoon |
| 7,172,576 | B2 * | 2/2007 | Sawa ................ A61M 25/0084 604/164.01 |
| 8,992,556 | B2 | 3/2015 | Chanduszko et al. |
| 2004/0044266 | A1 | 3/2004 | Siess et al. |
| 2006/0074398 | A1 | 4/2006 | Whiting et al. |
| 2007/0270741 | A1 * | 11/2007 | Hassett ............. A61M 25/0606 604/96.01 |
| 2009/0198153 | A1 | 8/2009 | Shriver |
| 2010/0016804 | A1 | 1/2010 | Muskatello et al. |
| 2011/0054487 | A1 | 3/2011 | Farnan |
| 2012/0071922 | A1 | 3/2012 | Shanley et al. |
| 2012/0179188 | A1 * | 7/2012 | Chanduszko ...... A61B 17/0057 606/185 |
| 2020/0376237 | A1 * | 12/2020 | Hayakawa ........ A61M 25/0662 |
| 2021/0393926 | A1 * | 12/2021 | Kondo ................ A61M 25/09 |

FOREIGN PATENT DOCUMENTS

| | | | |
|---|---|---|---|
| GB | 2 457 233 | A | 8/2009 |
| JP | 2006-271693 | A | 10/2006 |
| JP | 2013503693 | A | 2/2013 |
| JP | 2013537840 | A | 10/2013 |
| WO | 02/43791 | A1 | 6/2002 |
| WO | 2011/028310 | A1 | 3/2011 |
| WO | 2014/138216 | A1 | 9/2014 |
| WO | 2017/013123 | A1 | 1/2017 |

OTHER PUBLICATIONS

The extended European Search Report dated Dec. 4, 2020, by the European Patent Office in corresponding European Patent Application No. 18775498.1-1113. (7 pages).

Written Opinion of the International Searching Authority (PCT/ISA/237) dated Jul. 3, 2018 in International Application No. PCT/JP2018/012850, with English language translation (8 pages).

Office Action (First Office Action) dated Mar. 3, 2021, by the State Intellectual Property Office of People's Republic of China in corresponding Chinese Patent Application No. 201880022474.2 and an English Translation of the Office Action. (20 pages).

Office Action (Examination report No. 1 for standard patent application) dated Apr. 8, 2020, by the Australian Patent Office in corresponding Australian Patent Application No. 2018243038. (9 pages).

Office Action (Examination report No. 2 for standard patent application) dated Sep. 1, 2020, by the Australian Patent Office in corresponding Australian Patent Application No. 2018243038. (8 pages).

* cited by examiner

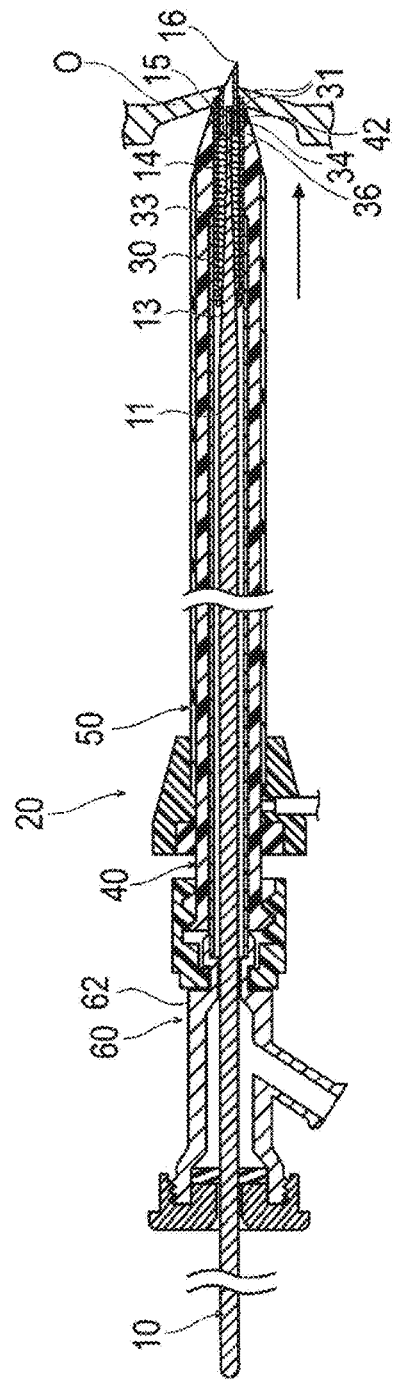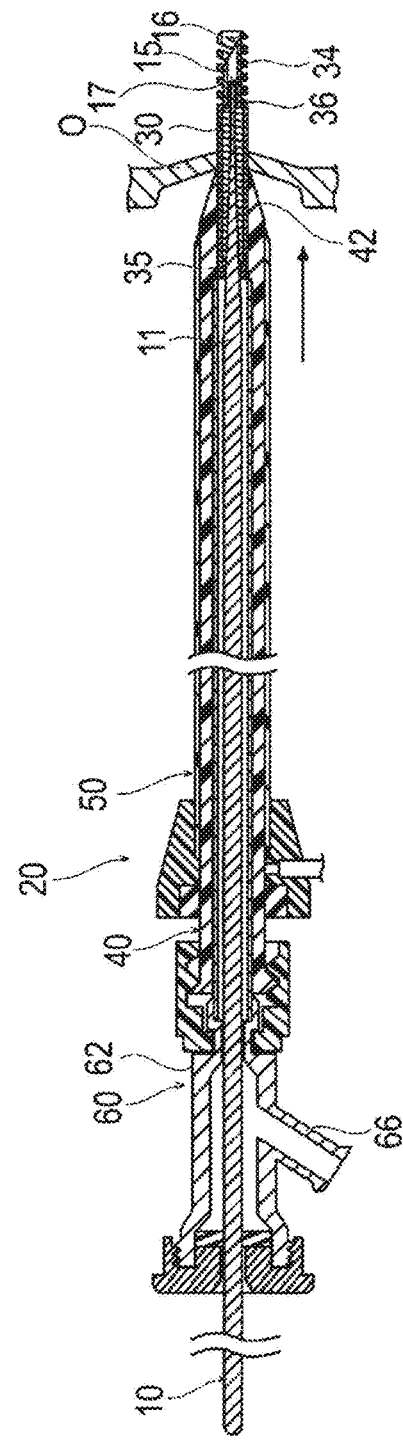
Fig. 8(A)
Fig. 8(B)

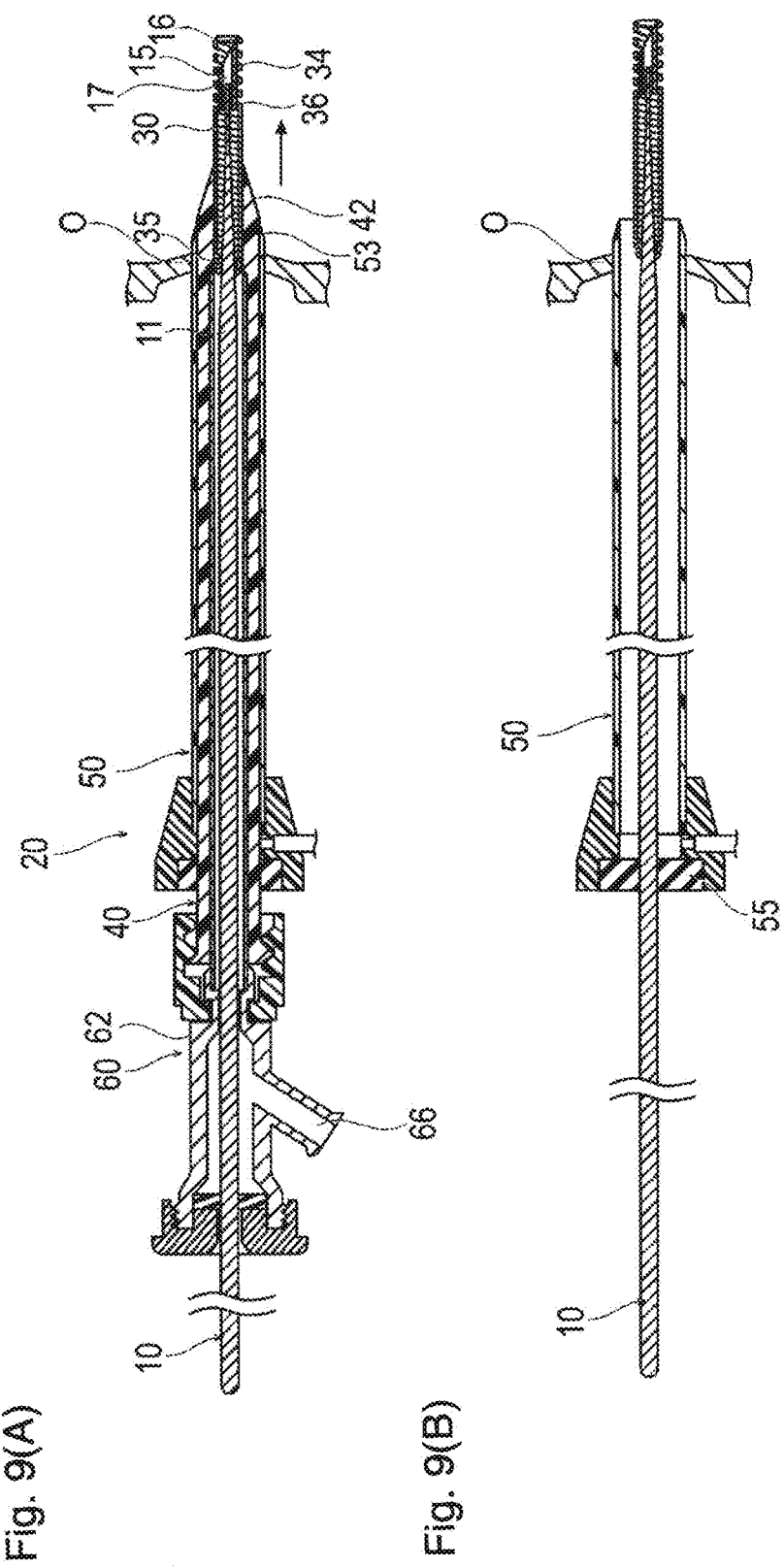

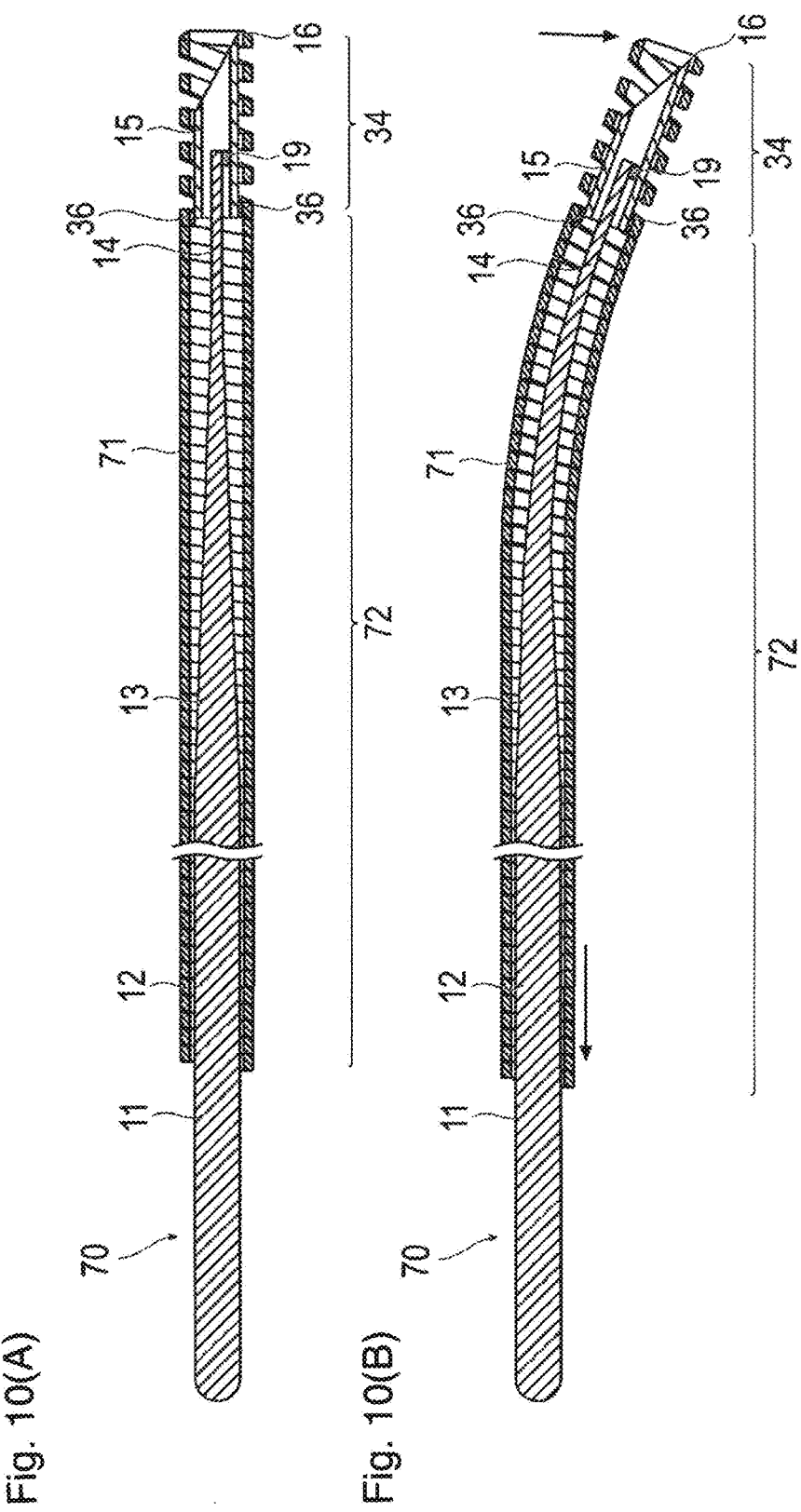

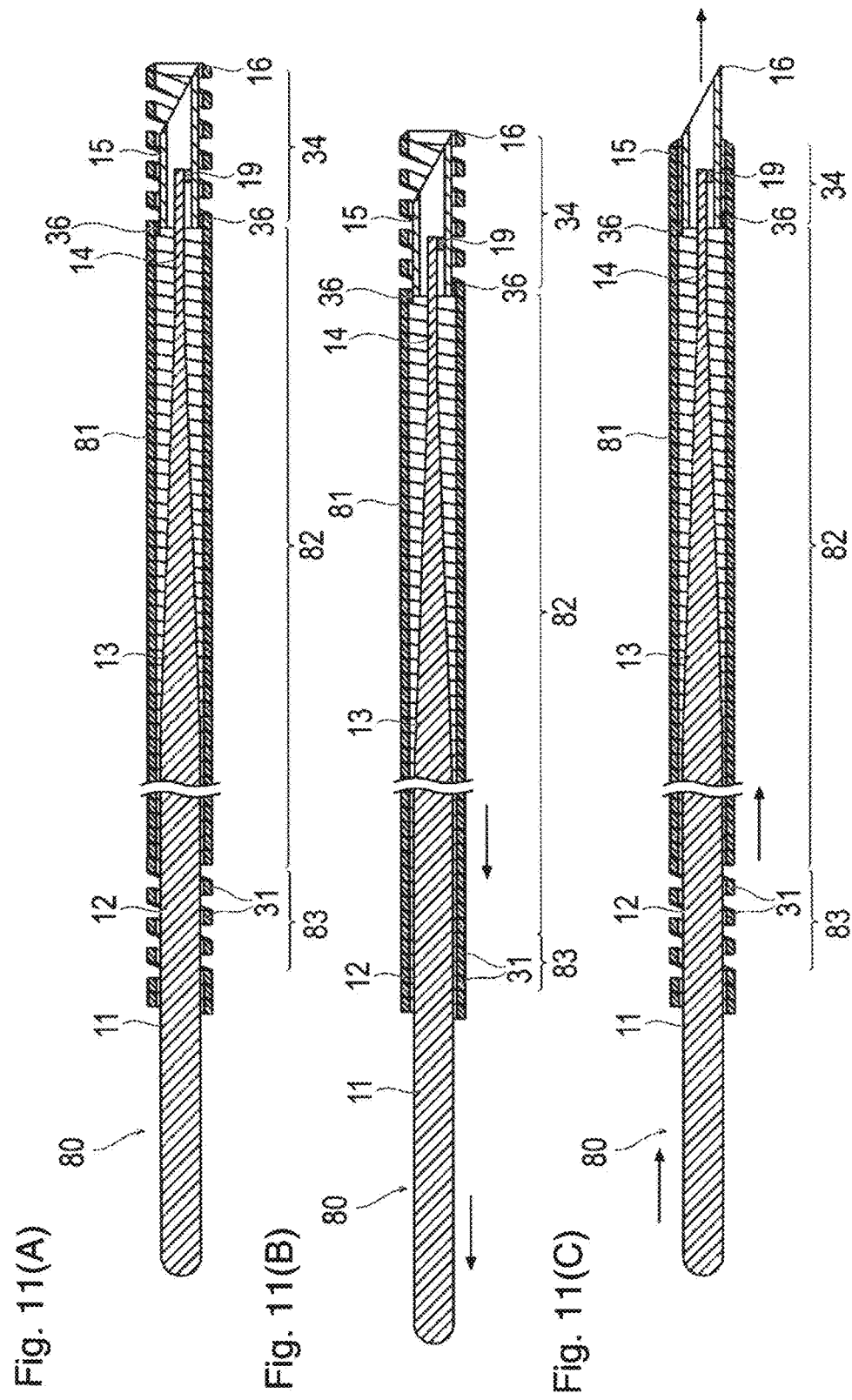

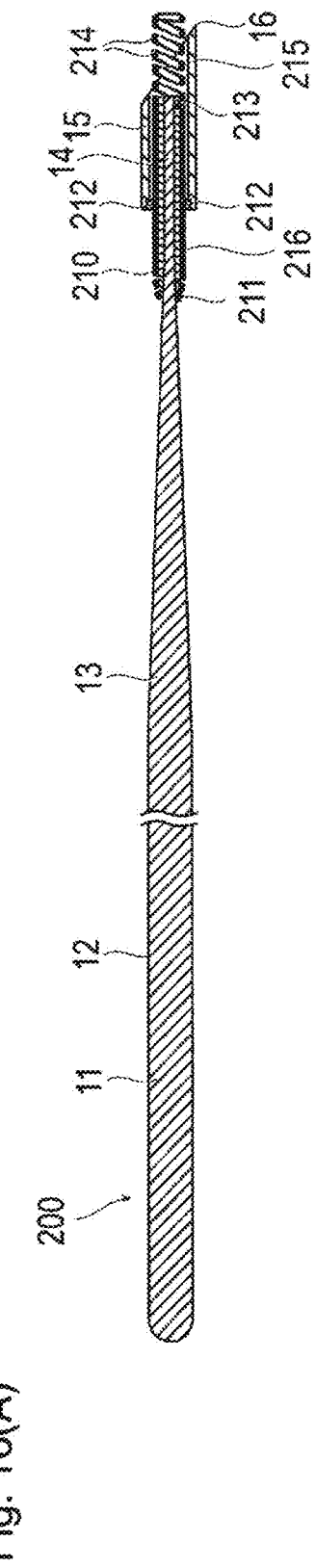
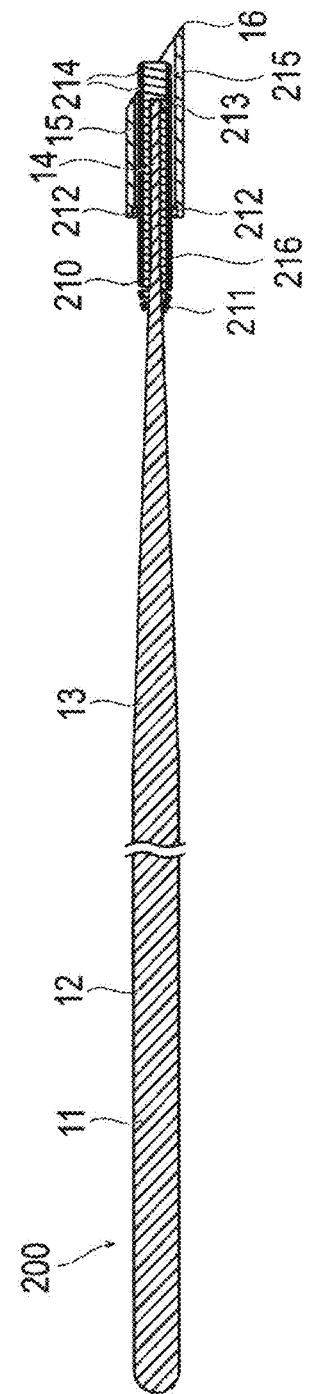

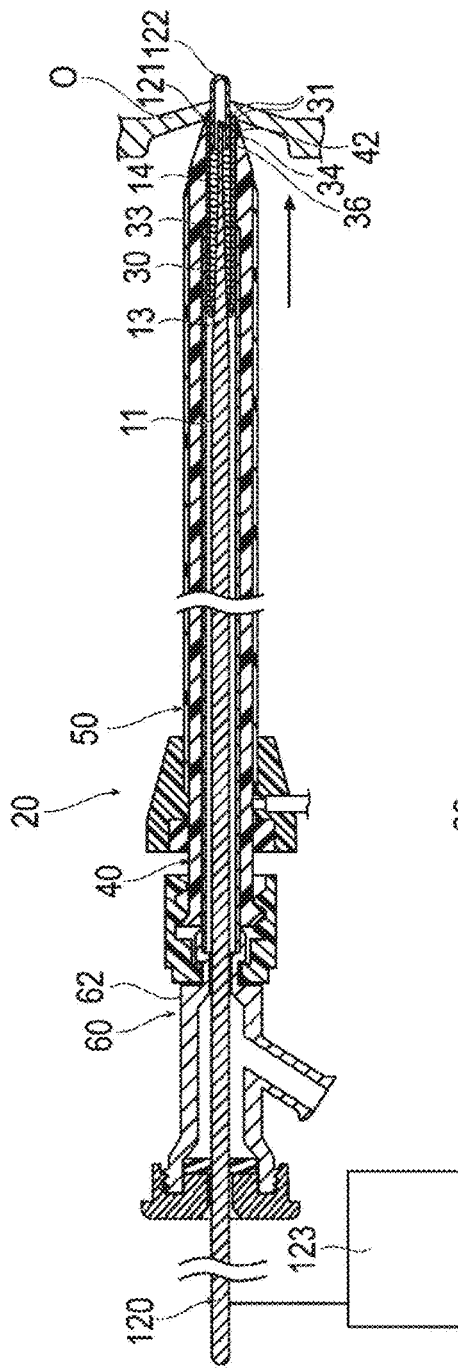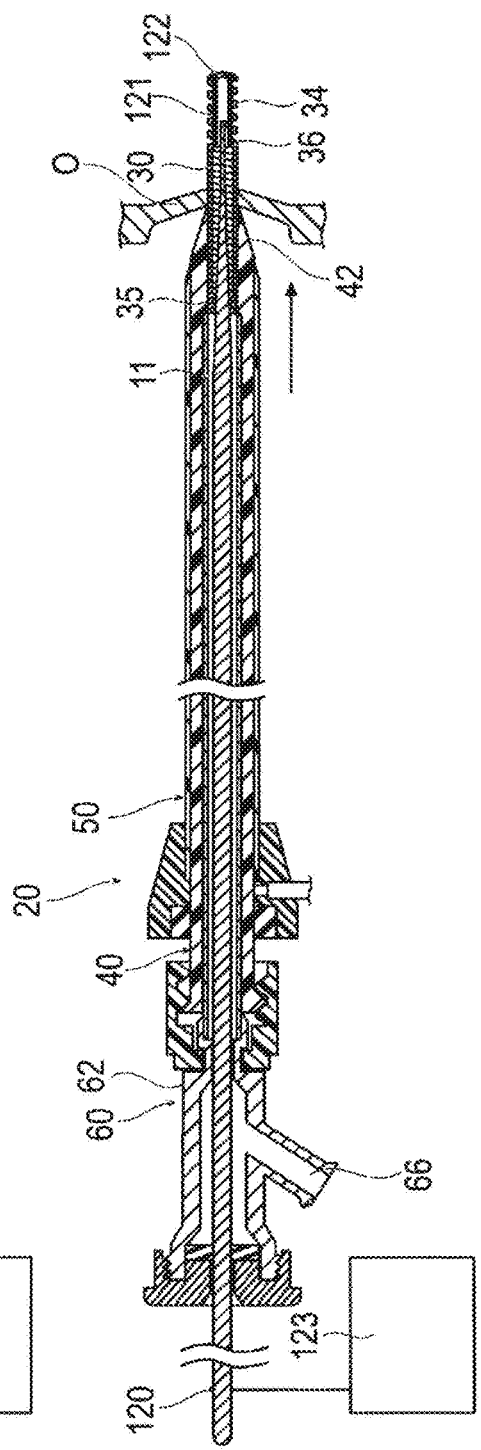
Fig. 18(A)
Fig. 18(B)

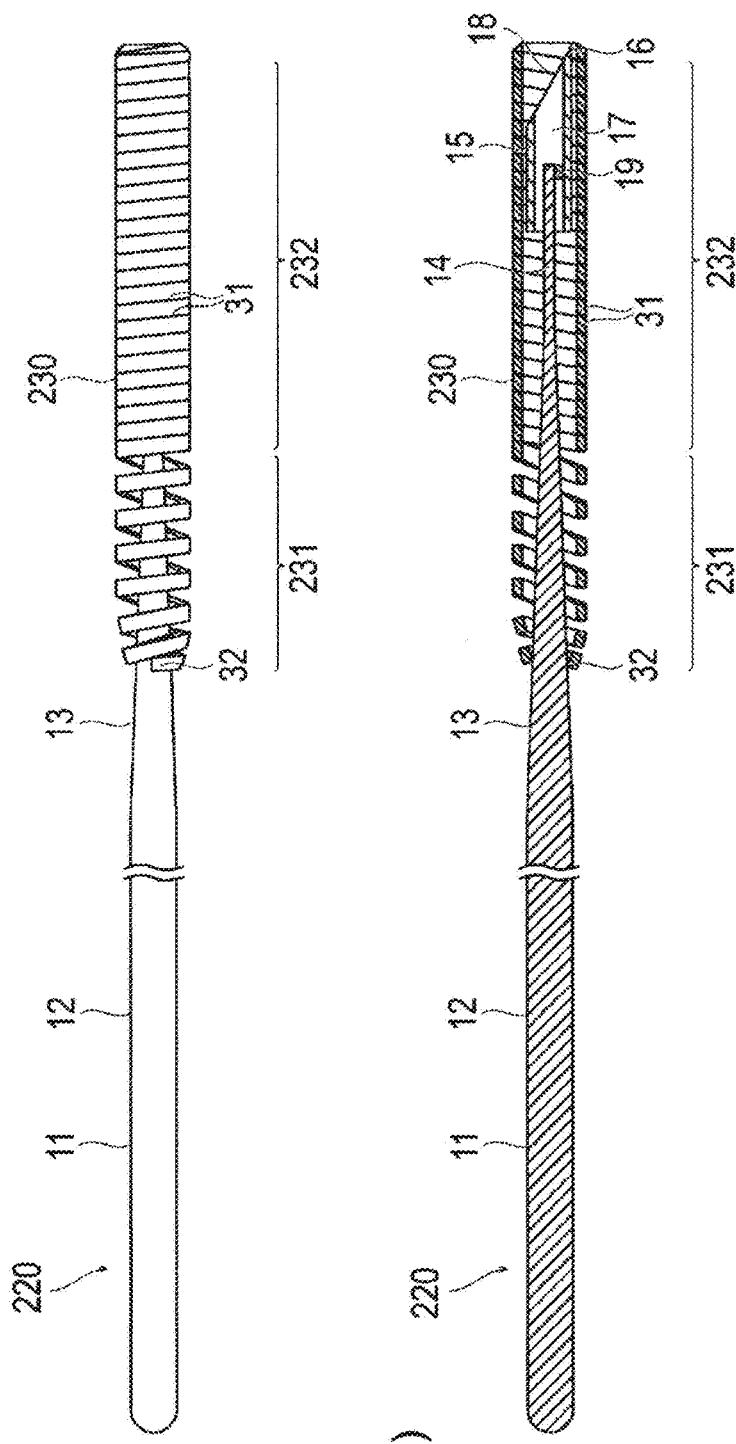

GUIDE WIRE, MEDICAL DEVICE, AND TREATMENT METHOD

CROSS-REFERENCES TO RELATED APPLICATIONS

This application is a continuation of International Application No. PCT/JP2018/012850 filed on Mar. 28, 2018, which claims priority to Japanese Application No. 2017-071873 filed on Mar. 31, 2017, the entire content of both of which is incorporated herein by reference.

TECHNICAL FIELD

The present invention generally relates to a guide wire, a medical device, and a treatment method for puncturing a biological tissue.

BACKGROUND DISCUSSION

In a heart, current flows in a myocardial tissue called a stimulation conduction system. In this manner, blood is circulated by the heart repeatedly contracting and expanding at proper timings. If an electrical signal flowing in the stimulation conduction system is abnormally generated or transmitted, the heart can no longer contract and expand at the proper timings, thereby resulting in arrhythmia.

As a method for treating the arrhythmia, a method is known in which a signal conduction path causing the arrhythmia is ablated and blocked by heating or cooling. As a device for performing this treatment method, a device is known which can be percutaneously inserted into a left atrium so as to ablate the signal conduction path located in an opening of a pulmonary vein. This ablation device is widely used since the ablation device is minimally invasive and can achieve excellent advantageous effect.

The mechanical puncture needle is used to perform the puncture using a sharp needle. If the mechanical puncture needle is used, the needle is excessively pressed, thereby causing a risk of erroneous puncture. If the erroneous puncture of the needle occurs, there is a possibility that the erroneous puncture may lead to a serious complication such as cardiac tamponade (condition where a heart failure occurs due to blood collected between a pericardium and a myocardium). On the other hand, the radio frequency energy puncture needle is used for a method of causing the radio frequency energy puncture needle to penetrate the atrial septum by outputting radio frequency energy supplied from a console serving as a separately provided device. Therefore, the radio frequency energy puncture needle has no risk of erroneous puncture. However, the radio frequency energy puncture needle is expensive, and requires the console.

U.S. Pat. No. 8,992,556 discloses a device in which an inner needle serving as the mechanical puncture needle is located inside an outer needle having a tubular shape. A distal end of the inner needle is bent so as to face a proximal side. The distal end of the inner needle is accommodated in the outer needle in a linearly extended state. The inner needle protrudes from the outer needle so as to open a hole in the atrial septum from the right atrium side. After reaching the left atrium, the inner needle is bent so as to face the proximal side. In this manner, the device disclosed in U.S. Pat. No. 8,992,556 prevents the inner needle from performing erroneous puncture.

SUMMARY

According to the inner needle of the device disclosed in U.S. Pat. No. 8,992,556, a needle distal end has an angle. Consequently, the inner needle meets strong resistance when passing through the outer needle. In addition, although the inner needle has the angle, the needle distal end is exposed. Accordingly, there is a possibility that the erroneous puncture may be performed by the sharp inner needle. In addition, a bent portion of the inner needle needs to have a decreased diameter so as to be more flexible than a proximal portion. Therefore, it is difficult to form a large diameter puncture hole in a biological tissue. Accordingly, a catheter is less likely to pass through the puncture hole.

Disclosed here is a guide wire, a medical device, and a medical method which can achieve satisfactory workability and can ensure safety by preventing a puncture needle portion from performing erroneous puncture.

According to one aspect, there is provided a guide wire for guiding an elongated tubular body that is configured to be inserted into a living body. The guide wire comprises a flexible and elongated shaft portion possessing a distal portion, a puncture portion located at the distal portion of the shaft portion to form a hole in a first biological tissue, and a deformable deformation portion fixed to the shaft portion or the puncture portion and positioned to cover the shaft portion or the puncture portion, with the deformation portion being positionable inside the elongated tubular body and restricting deflection of the distal portion of the shaft portion.

According to another aspect, there is provided a guide wire for guiding an elongated tubular body that is configured to be inserted into a living body. The guide wire comprises a flexible and elongated shaft portion possessing a distal portion, a puncture portion located at the distal portion of the shaft portion to form a hole in a biological tissue, a deformable deformation portion fixed to the shaft portion or the puncture portion and positioned in covering relation to the puncture portion, with the distal end of the deformation portion being movable into contact with the biological tissue while the deformation portion is located outside the elongated body and receiving a force acting in a proximal direction when the distal end of the deformation portion is moved into contact with the biological tissue while the deformation portion is located outside the elongated body that causes the deformation portion to deflect together with the distal portion of the shaft portion while still covering the puncture portion.

According to still another aspect of the disclosure here there is provided a guide wire for guiding an elongated tubular body that is configured to be inserted into a living body, wherein the guide wire comprises: a flexible and elongated shaft portion possessing a distal portion, a puncture portion located at the distal portion of the shaft portion and configured to puncture a first biological tissue and form a hole in the first biological tissue, the puncture portion possessing a distal end; an axially expandable and contractable cover portion covering a distal end of the puncture portion; the puncture portion being exposed outside the cover portion during the puncturing of the first biological tissue, the distal end of the puncture portion being covered by the cover portion after the puncturing of the first biological tissue so as not to puncture second biological tissue different from the first biological tissue.

According to a further aspect there is provided a medical device for forming a hole in a biological tissue inside a living body. The medical device includes a tubular elongated body to be inserted into the living body, and a guide wire insertable into the elongated body. The guide wire has a flexible and elongated shaft portion, a puncture portion located in a distal portion of the shaft portion, and having a distal side provided with a needle portion for forming a hole in a biological tissue, and a deformable deformation portion fixed to the shaft portion or the puncture portion. The deformation portion located inside the elongated body restricts deflection of the distal portion of the shaft portion.

According to another aspect, there is provided a treatment method for forming a hole in biological tissue inside a living body using a medical device. The treatment method involves accommodating a needle portion and a deformation portion of a guide wire in an elongated body so that the distal end of the elongated body is brought into contact with the biological tissue, moving the guide wire to the distal side or in the distal direction with respect to the elongated body, and pressing the distal end of the puncture portion or the deformation portion against the biological tissue so that the needle portion forms the hole in the biological tissue, and moving the elongated body along the guide wire.

There is also provided a treatment method for forming a hole in biological tissue inside a living body. The treatment method involves accommodating a puncture portion and a cover portion of a guide wire in an elongated body so that a distal end of the elongated body is brought into contact with the biological tissue, moving the guide wire to a distal side with respect to the elongated body, pressing a distal end of the cover portion against the biological tissue so that the cover portion shrinks in an axial direction, and causing the puncture portion exposed from the cover portion to form the hole in the biological tissue, pushing the cover portion into the hole of the biological tissue subsequently to the puncture portion so that the cover portion covers the puncture portion, and moving the elongated body along the guide wire.

According to the guide wire, the medical device, and the treatment method which are configured as described above, in a state where the deformation portion is accommodated in the elongated body, the elongated body and the deformation portion restrict the deflection of the distal portion of the shaft portion. In this manner, the hole can be formed in the biological tissue by the puncture portion. In this way, while the guide wire functions as a guide wire for guiding the elongated body, the hole can be formed in the biological tissue. Then, since the guide wire does not need a separate device having a puncture function, the guide wire shows satisfactory workability. In addition, the guide wire can ensure safety by preventing the puncture needle portion from performing erroneous puncture.

BRIEF DESCRIPTION OF DRAWINGS

FIG. 3(A) is a plan view, and FIG. 3(B) is a sectional view.

FIG. 7(A) illustrates a state where a sheath assembly is inserted into a right atrium along the guide wire, and FIG. 7(B) illustrates a state where a dilator is pressed against a fossa ovalis (oval fossa).

FIGS. 8(A) and 8(B) are sectional views illustrating a state when puncture is performed by the medical device. FIG. 8(A) illustrates a state where a puncture portion punctures the fossa ovalis, and FIG. 8(B) illustrates a state where the puncture portion is accommodated in a deformation portion.

FIGS. 9(A) and 9(B) are sectional views illustrating a state when puncture is performed by the medical device. FIG. 9(A) illustrates a state where the sheath assembly is inserted into a hole of the fossa ovalis, and FIG. 9(B) illustrates a state where the dilator and an inserter are pulled out of an outer sheath.

FIGS. 10(A) and 10(B) are sectional views illustrating a first modification example. FIG. 10(A) illustrates a state before the guide wire is bent, and FIG. 10(B) illustrates a state when the guide wire is bent.

FIGS. 11(A), 11(B) and 11(C) are sectional views illustrating a second modification example. FIG. 11(A) illustrates a state before the deformation portion of the guide wire shrinks, FIG. 11(B) illustrates a state where a second sparse pitch portion of the deformation portion of the guide wire shrinks, and FIG. 11(C) illustrates a state where the guide wire is moved to a distal side due to a stretching force of the second sparse pitch portion.

FIG. 12(A) illustrates a third modification example, and FIG. 12(B) illustrates a fourth modification example.

FIG. 13(A) illustrates a state before the deformation portion of the guide wire shrinks in an axial direction, and FIG. 13(B) illustrates a state where the deformation portion of the guide wire shrinks in the axial direction.

FIG. 14(A) illustrates a sixth modification example, and FIG. 14(B) illustrates a seventh modification example.

FIG. 15(A) illustrates an eighth modification example, and FIG. 15(B) illustrates a ninth modification example.

FIGS. 16(A) and 16(B) are sectional views illustrating a tenth modification example. FIG. 16(A) illustrates a state before the deformation portion of the guide wire shrinks in the axial direction, and FIG. 16(B) illustrates a state where the deformation portion of the guide wire shrinks in the axial direction.

FIGS. 18(A) and 18(B) are sectional views illustrating a state where puncture is performed according to the eleventh modification example. FIG. 18(A) illustrates a state where the puncture portion punctures the fossa ovalis, and FIG. 18(B) illustrates a state where the puncture portion is accommodated in the deformation portion.

FIGS. 19(A) and 19(B) are views illustrating a guide wire according to a twelfth modification example. FIG. 19(A) is a plan view, and FIG. 19(B) is a sectional view.

FIG. 20(A) illustrates a state where a hole is formed in the fossa ovalis by the puncture portion, and FIG. 20(B) illustrates a state where the deformation portion covers the puncture portion.

FIG. 22(A) illustrates a state before the deformation portion of the guide wire shrinks in the axial direction, and FIG. 22(B) illustrates a state where the deformation portion of the guide wire shrinks in the axial direction.

FIG. 23(A) is a plan view, and FIG. 23(B) is a sectional view.

FIG. 24(A) illustrates a state where the deformation portion of the guide wire according to the fourteenth modification example shrinks in the axial direction, and FIG. 24(B) illustrates a state where the deformation portion of the guide wire according to a fifteenth modification example shrinks in the axial direction.

FIG. 25(A) illustrates a state before the deformation portion of the guide wire shrinks in the axial direction, and FIG. 25(B) illustrates a state where the deformation portion of the guide wire shrinks in the axial direction.

FIG. 26(A) illustrates a state before the deformation portion of the guide wire shrinks in the axial direction, and FIG. 26(B) illustrates a state where the deformation portion of the guide wire shrinks in the axial direction.

DETAILED DESCRIPTION

Figure 1:
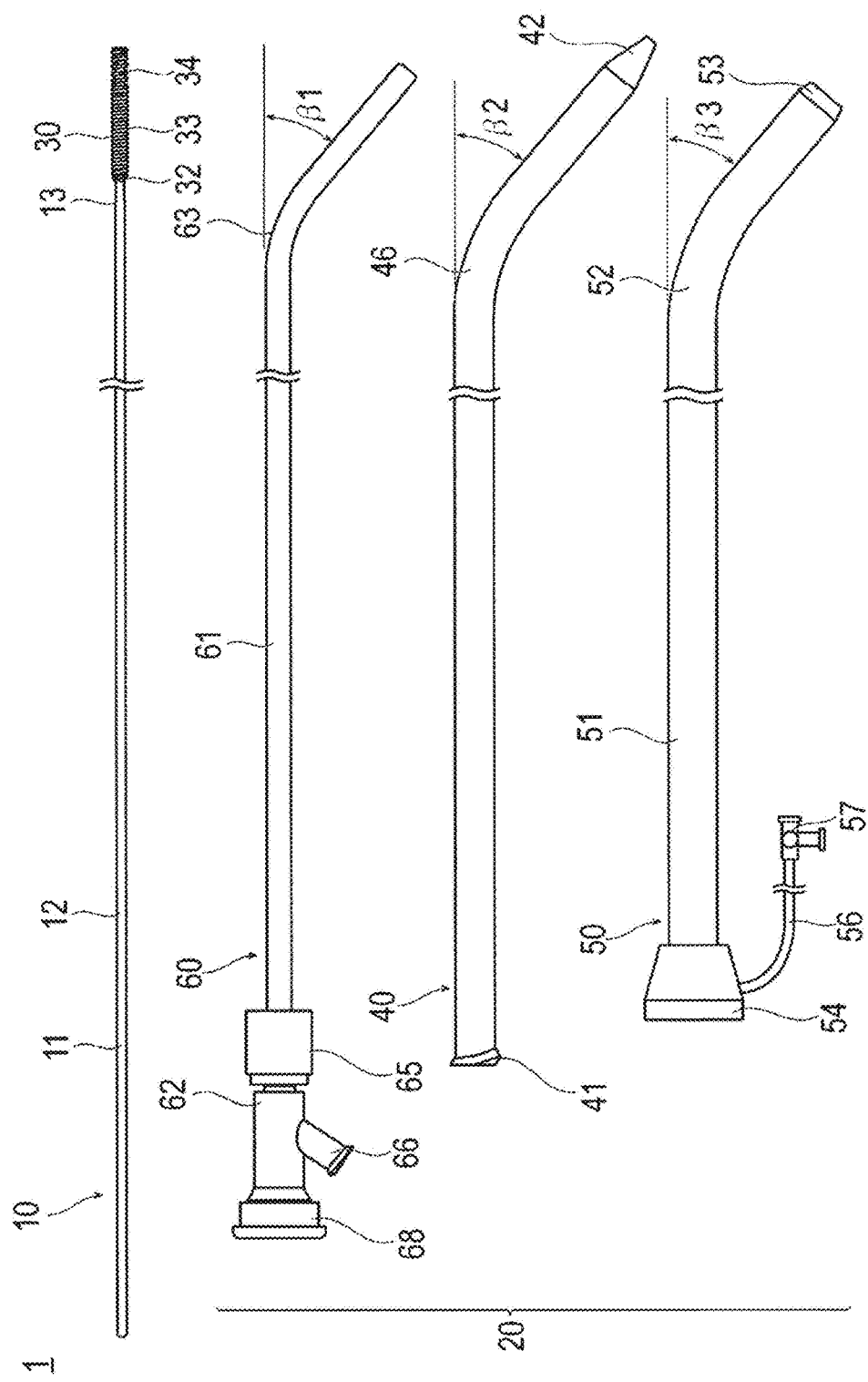
FIG. 1 is a plan view illustrating a medical device according to an embodiment.

Set forth below with reference to the accompanying drawings is a detailed description of embodiments of a guide wire, a medical device, and a treatment method involving puncturing biological tissue representing examples of the inventive guide wire, medical device, and treatment method disclosed here. Dimensional proportions in the drawings are exaggerated and different from actual proportions for convenience of description and understanding, in some cases. In the description below, a side or end of a device which is inserted into a blood vessel will be referred to as a "distal side" or "distal end", and an operator's hand side will be referred to as a "proximal side" or "proximal end".

A medical device 1 according to one embodiment disclosed here is used for forming a hole which leads from a right atrium R to a left atrium L (refer to FIG. 6) in an fossa ovalis O by a guide wire 10 having a puncture function. In a case where there is the hole in the fossa ovalis O, an ablation catheter percutaneously inserted into a vena cava is guided to the right atrium R. Thereafter, the ablation catheter is inserted into the left atrium L via the hole, and a periphery of an opening of a pulmonary vein can be ablated. That is, the medical device 1 is a device for forming an access route of the ablation catheter to the fossa ovalis.

As illustrated in FIGS. 1 to 4, the medical device 1 includes a guide wire 10 having a puncture function and a sheath assembly 20 into which the guide wire 10 is inserted during use. The sheath assembly 20 has an inserter 60 into which the guide wire 10 is inserted, a dilator 40 into which the inserter 60 is inserted, and an outer sheath 50 into which the dilator 40 is inserted.

The guide wire 10 is an elongated device for guiding the sheath assembly 20 including the dilator 40 or the ablation catheter to a desired position inside the blood vessel. Furthermore, the guide wire 10 is also provided with a function to puncture the fossa ovalis O. The guide wire 10 includes an elongated shaft portion 11, a puncture portion 15 including a sharp needle portion 16, and a deformation portion 30 for accommodating the puncture portion 15. The shaft portion 11 is an elongated wire rod, and includes a shaft proximal portion 12 located on the proximal side or proximal end portion, a shaft distal portion 14 located on the distal side or distal end portion, and a shaft diameter decreasing portion 13 located between the shaft proximal portion 12 and the shaft distal portion 14. The shaft proximal portion 12 is a portion having a constant outer diameter. The shaft diameter decreasing portion 13 extends from the shaft proximal portion 12 toward the distal side, and is a portion whose outer diameter decreases in a tapered shape. As the shaft diameter decreasing portion 13 has the outer diameter decreasing in the tapered shape, a physical property such as flexural rigidity is gradually changed along the axial direction of the shaft diameter decreasing portion 13. Therefore, the shaft diameter decreasing portion 13 can prevent kinks which are likely to occur due to a rapid change in the physical property. In addition, the flexural rigidity of the shaft diameter decreasing portion 13 gradually decreases along the axial direction of the shaft diameter decreasing portion 13. Accordingly, the shaft portion 11 can be satisfactorily pushed into a meandering blood vessel so that the shaft portion 11 can easily reach the blood vessel. The shaft distal portion 14 is a portion extending from the shaft diameter decreasing portion 13 to the distal side and having a constant outer diameter. The outer diameter of the shaft distal portion 14 is smaller than the outer diameter of the shaft proximal portion 12. The outer diameter of the shaft distal portion 14 may not be constant.

A material from which the shaft portion 11 is fabricated may preferably be a material which is flexible and hard to some extent. For example, it is possible to preferably use metal such as stainless steel, tantalum, titanium, platinum, gold, and tungsten, a shape memory alloy that exhibits a shape memory effect or super-elasticity when heated, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide. As the shape memory alloy, it is possible to preferably use a Ni—Ti alloy, a Cu—Al—Ni alloy, or a Cu—Zn—Al alloy. In addition, the shaft portion 11 may contain an X-ray contrast material. For example, the X-ray contrast material is preferably formed of at least one metal or two or more alloys in groups including gold, platinum, iridium, tungsten or an alloy thereof, and a silver-palladium alloy.

By way of example, in the axial direction, the shaft portion 11 may have a length of 300 to 5,000 mm, preferably 1,000 to 3,000 mm, and more preferably 1,500 to 2,500 mm. By way of example, the outer diameter of the shaft distal portion 14 may be 0.04 to 0.8 mm, preferably 0.08 to 0.4 mm, and more preferably 0.12 to 0.2 mm. As an example, the outer diameter of the shaft proximal portion 12 may be 0.3 to 1.0 mm, preferably 0.4 to 0.8 mm, and more preferably 0.5 to 0.6 mm.

The puncture portion 15 is a cylindrical tube with a circular cross-section having the sharp needle portion 16 for piercing biological tissue. The puncture portion 15 includes a through-hole 17 penetrating or extending from the proximal side to the distal side. The puncture portion 15 is fixed to a distal portion of the shaft portion 11. The distal end of the puncture portion 15 includes an inclined surface 18 inclined to a central axis. A most distal side portion of the inclined surface 18 is the sharp needle portion 16 for puncturing the biological tissue. A distal end of the shaft distal portion 14 is located inside the puncture portion 15. The distal end of the shaft distal portion 14 is fixed to an inner peripheral surface of the puncture portion 15 through welding or bonding by a needle fixing portion 19. The inner diameter of the puncture portion 15 is larger than the outer diameter of the shaft distal portion 14. Then, the needle fixing portion 19 is disposed only in a portion of the shaft distal portion 14 in a circumferential direction. Therefore, the shaft distal portion 14 and the needle fixing portion 19 do not inhibit fluid from flowing inside the puncture portion 15. A plurality of the needle fixing portions 19 may be provided. In addition, it is preferable that an axial center of the puncture portion 15 and an axial center of the shaft distal portion 14 substantially coincide with each other. The axial center of the puncture portion 15 and the axial center of the shaft distal portion 14 may not coincide with each other. A shape of the needle portion 16 of the puncture portion 15 is not particularly restricted as long as the biological tissue can be punctured. For example, the needle portion 16 may be a conical or knife-shaped flat plate, or a shovel-shaped curved plate. Therefore, the puncture portion 15 may not have the through-hole 17. In addition, a cross-sectional shape of the puncture portion 15 may not be a circular shape. In addition, the puncture portion may have a structure integrated with the shaft portion.

The length in the axial direction of the puncture portion 15 is preferably set to such an extent that the length does not inhibit flexibility of the guide wire 10 inside the blood vessel. By way of example, the length in the axial direction of the puncture portion 15 may be 2 to 10 mm, preferably 3 to 8 mm, and more preferably 4 to 6 mm. By way of example, the outer diameter of the puncture portion 15 may be 0.3 to 1.0 mm, preferably 0.4 to 0.8 mm, and more preferably 0.5 to 0.6 mm. By way of example, the inner diameter of the puncture portion 15 may be 0.1 to 0.9 mm, preferably 0.2 to 0.7 mm, and more preferably 0.3 to 0.5 mm. An inclination angle $\alpha 1$ of the puncture portion 15 with respect to the central axis of the inclined surface 18 is appropriately set. For example, the inclination angle $\alpha 1$ may be 3 to 45 degrees, preferably 5 to 40 degrees, and more preferably 10 to 35 degrees.

A material which may be used to fabricate the puncture portion 15 is preferably a material which is hard to some extent. For example, it is possible to preferably use metal such as stainless steel, tantalum, titanium, platinum, gold, and tungsten, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide. In addition, the puncture portion 15 may contain the X-ray contrast material. For example, the X-ray contrast material is preferably formed of at least one metal or two or more alloys in groups including gold, platinum, iridium, tungsten or an alloy thereof, and a silver-palladium alloy. A surface of the puncture portion 15 can be coated with silicone or a hydrophilic material.

As a whole, the deformation portion 30 is a tubular and elastically deformable member for accommodating the puncture portion 15 so that the puncture portion 15 can protrude from or distally beyond the deformation portion 30. The deformation portion 30 is formed using a spirally wound wire rod 31. An end portion of the wire rod 31 on the distal side of the wire rod 31 may be brazed to fill a gap between the adjacent windings of the wire rod 31 in order to prevent damage to the biological tissue when in contact. Alternatively, adjacent windings of the wire rod 31 may be welded by bringing the adjacent windings of the wire rod 31 into contact with each other. Thereafter, an outer edge portion may be subjected to curved surface processing, and may be smoothly formed. The deformation portion 30 includes a dense pitch portion 33 where an inter-pitch distance of the spiral is short, a sparse pitch portion 34 where the inter-pitch distance of the spiral is longer or greater than in the dense pitch portion 33, and a proximal diameter decreasing portion 35 to be fixed to the shaft portion 11. The inter-pitch distance is a movement distance in the axial direction when the spiral is wound 360 degrees in the circumferential direction. That is, the inter-pitch distance is the axial distance between common points on axially adjacent windings. The sparse pitch portion 34, the dense pitch portion 33, and the proximal diameter decreasing portion 35 are formed using one continuous wire rod 31. The sparse pitch portion 34, the dense pitch portion 33, and the proximal diameter decreasing portion 35 may be formed using a plurality of wire rods. In addition, the wire rod 31 may not have the dense pitch portion 33 spirally wound without any gap. That is, the dense pitch portion 33 may be eliminated so that the wire rod 31 is configured to include only sparse pitches. In addition, the deformation portion 30 may be formed using an elastically deformable resin tube or a mesh tube braided with the wire rod. At least a portion of the mesh tube may be incorporated or may not be incorporated in the resin tube.

The dense pitch portion 33 is formed using a wire rod 31 spirally wound so that the windings are adjacent to each other without any gap. The dense pitch portion 33 has substantially constant outer diameter and inner diameter along the axial direction. The dense pitch portion 33 surrounds the distal portion of the shaft diameter decreasing portion 13 and the proximal portion of the shaft distal portion 14. The axial center of the spiral of the dense pitch portion 33 substantially coincides with the axial center of the shaft diameter decreasing portion 13 and the shaft distal portion 14. The inner diameter of the dense pitch portion 33 is larger than the outer diameter of the shaft portion 11 located inside the dense pitch portion 33. Therefore, a flow path for circulating the fluid is formed between the shaft portion 11 and the dense pitch portion 33. So long as the inter-pitch distance of the dense pitch portion 33 is shorter than that of the sparse pitch portion 34, the dense pitch portion 33 may have a gap between the axially adjacent windings of the wire rod 31 aligned with each other in the axial direction. In addition, the inter-pitch distance of the dense pitch portion 33 and the inter-pitch distance of the sparse pitch portion 34 may coincide (i.e., may be equal) with each other. Alternatively, the inter-pitch distance of the dense pitch portion 33 may be longer or greater than the inter-pitch distance of the sparse pitch portion 34. The distal portion of the dense pitch portion 33 has a second fixing portion 36 to be fixed through welding or adhesion to an outer peripheral surface of an end portion on the proximal side of the puncture portion 15. The second fixing portion 36 is disposed in the most distal portion (boundary portion between the dense pitch portion 33 and the sparse pitch portion 34) of the dense pitch portion 33, or in a portion close to the most distal portion of the dense pitch portion 33.

The sparse pitch portion 34 is formed using the wire rod 31 spirally wound while being adjacent to each other with a gap. The sparse pitch portion 34 has substantially constant outer diameter and inner diameter along the axial direction. The sparse pitch portion 34 surrounds the puncture portion 15 and a portion of the shaft distal portion 14 located inside the puncture portion 15. The axial center of the spiral of the sparse pitch portion 34 substantially coincides with the axial center of the puncture portion 15 and the shaft distal portion 14. As illustrated in FIG. 8(A), the sparse pitch portion 34 can shrink in the axial direction so as to decrease a gap between the axially adjacent windings of the wire rod 31 aligned with each other in the axial direction. If the sparse pitch portion 34 shrinks in the axial direction, the needle portion 16 of the puncture portion 15 accommodated inside the sparse pitch portion 34 protrudes to the distal side. The inner diameter of the sparse pitch portion 34 is slightly larger than the outer diameter of the puncture portion 15. In this manner, the deformation of the sparse pitch portion 34 in the axial direction is not inhibited by a friction force with the puncture portion 15. The inner peripheral surface of the sparse pitch portion 34 may be in contact with or may not be in contact with the outer peripheral surface of the puncture portion 15. An end surface on the distal side of the sparse pitch portion 34 decreases in diameter in a tapered shape toward the distal side.

As illustrated in FIG. 3, the proximal diameter decreasing portion 35 is formed by spirally winding the wire rod 31 so that the axially adjacent windings are adjacent to each other with a gap between axially adjacent windings. The proximal diameter decreasing portion 35 has the outer diameter and the inner diameter which decrease from the dense pitch portion 33 toward the proximal side. The proximal diameter decreasing portion 35 surrounds a partial portion or a whole portion of the shaft diameter decreasing portion 13. The axial center of the spiral of the proximal diameter decreasing portion 35 substantially coincides with the axial center of the shaft diameter decreasing portion 13. The inner diameter of the proximal diameter decreasing portion 35 is larger than the outer diameter of the shaft portion 11 located inside the proximal diameter decreasing portion 35 except for the proximal side end portion. Therefore, a flow path for circulating the fluid is formed between the shaft portion 11 and the proximal diameter decreasing portion 35. The proximal side end portion of the proximal diameter decreasing portion 35 is fixed to the shaft diameter decreasing portion 13 of the shaft portion 11 through welding or bonding. A gap between the windings of the wire rod 31 adjacent to each other in the proximal diameter decreasing portion 35 enables the fluid to be circulated between the outer peripheral surface side and the inner peripheral surface side of the proximal diameter decreasing portion 35. The windings of the wire rod 31 adjacent to each other in the proximal diameter decreasing portion 35 may be in contact with each other without any gap. In addition, a configuration of the proximal diameter decreasing portion 35 is not particularly restricted. Therefore, the proximal diameter decreasing portion 35 may not have a spiral shape. Therefore, the proximal diameter decreasing portion 35 may be a solder joint portion for joining the sparse pitch portion 34 and the shaft portion 11 to each other.

A cross-sectional shape orthogonal to the extending direction of the wire rod 31 in the wire rod 31 forming the deformation portion 30 is a rectangular shape (or square shape). Therefore, if the deformation portion 30 shrinks in the axial direction, the windings of the wire rod 31 aligned with each other in the axial direction come into contact with a wide area. Therefore, the deformation portion 30 shrunk in the axial direction shows excellent ability to transmit the force in the axial direction. The cross-sectional shape of the wire rod 31 forming the deformation portion 30 may not be the rectangular shape or the square shape, and may be a circular shape, an elliptical shape, a parallelogram shape, or a trapezoidal shape.

Figures 3A, 3B:
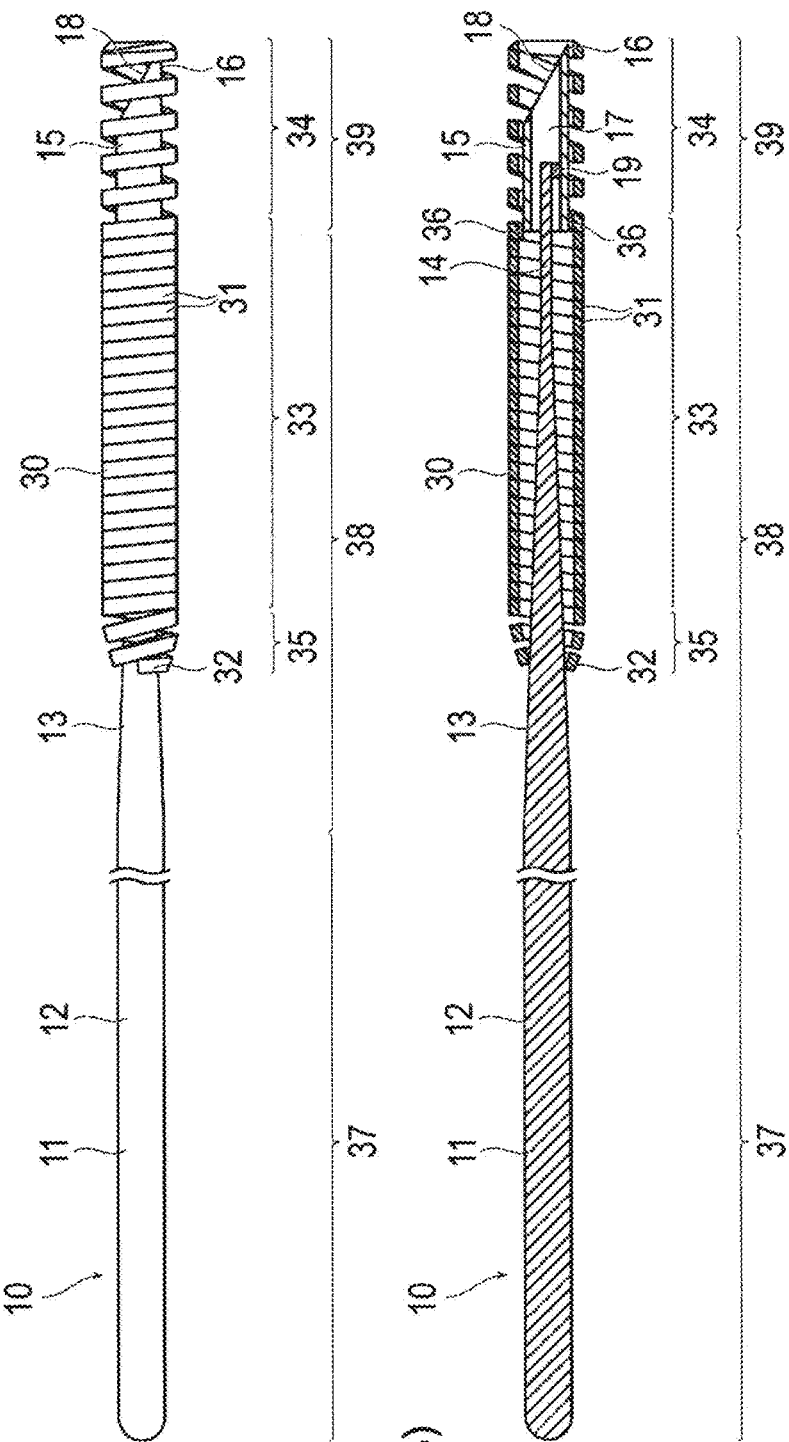
FIGS. 3(A) and 3(B) are views illustrating a guide wire.

The guide wire 10 is linear without being bent in a natural state where no external force is applied thereto. That is, in the absence of any load/force applied to the guide wire 10, the guide wire is linear or straight. Referring to FIGS. 3(A) and 3(B), the guide wire 10 is comprised of a guide wire proximal portion 37, a guide wire intermediate portion 38, and a guide wire distal portion 39 so that all of these are aligned with each other in the axial direction from the proximal side or proximal end toward the distal side or distal end. The guide wire proximal portion 37 is configured to include the shaft proximal portion 12 having a constant outer diameter. The guide wire intermediate portion 38 is configured to include a part of the shaft portion 11 and a part of the deformation portion 30 which are located on the proximal side from the proximal end of the puncture portion 15 and on the distal side from the proximal end of the shaft diameter decreasing portion 13. The guide wire distal portion 39 is configured to include the puncture portion 15, a distal end portion of the deformation portion 30, and a distal end portion of the shaft portion 11 which are located on the distal side from the proximal end of the puncture portion 15. The guide wire distal portion 39 has a larger outer diameter than the guide wire proximal portion 37 and a portion of the guide wire intermediate portion 38. The guide wire distal portion 39 has higher flexural rigidity than the guide wire intermediate portion 38. The guide wire proximal portion 37 has a larger outer diameter than a proximal portion of the guide wire intermediate portion 38. The guide wire proximal portion 37 has higher flexural rigidity than a portion of the guide wire intermediate portion 38. The length of the guide wire 10 is appropriately set, and may be 300 to 5,000 mm, for example.

The deformation portion 30 is formed by spirally winding the linear wire rod 31. Alternatively, the deformation portion 30 may be cut out of a circular or cylindrical tube by performing laser processing.

A material used to fabricate the deformation portion 30 is preferably a material which is elastically deformable and hard to some extent. For example, it is possible to preferably use a shape memory that exhibits a shape memory effect or super-elasticity when heated, metal such as stainless steel, tantalum, titanium, platinum, gold, and tungsten, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide. As the shape memory alloy, it is possible to preferably use a Ni—Ti alloy, a Cu—Al—Ni alloy, or a Cu—Zn—Al alloy. In addition, the deformation portion 30 may contain the X-ray contrast material. For example, the X-ray contrast material is preferably formed of at least one metal or two or more alloys in groups including gold, platinum, iridium, tungsten or an alloy thereof, and a silver-palladium alloy. In addition, the deformation portion 30 is formed into a spiral shape. Accordingly, irregularities are increased so that the deformation portion 30 can have an improved ultrasound contrast effect.

In general, the guide wire 10 has excellent flexibility while having rigidity to some degree so that an inserting target biological lumen is not damaged and the guide wire 10 can be pushed forward into the meandering biological lumen. Therefore, in a state where the deflection (deformation in the radial direction) is not restricted, if the distal end of the deformation portion 30 in the guide wire 10 according to the present embodiment receives the force acting toward the proximal side, some portions of the guide wire 10 are deflected, and the force escapes or is transferred to other portions from the distal portion of the deformation portion 30. Therefore, even if the distal end of the deformation portion 30 receives the force acting toward the proximal side, the force required for the deformation portion 30 to shrink in the axial direction does not act on the deformation portion 30. Therefore, in a state where the deformation portion 30 is freely deflected, the distal end of the deformation portion 30 receives the force acting toward the proximal side, the deformation portion 30 is deflected, and maintains a state of accommodating the needle portion 16.

Figure 2:
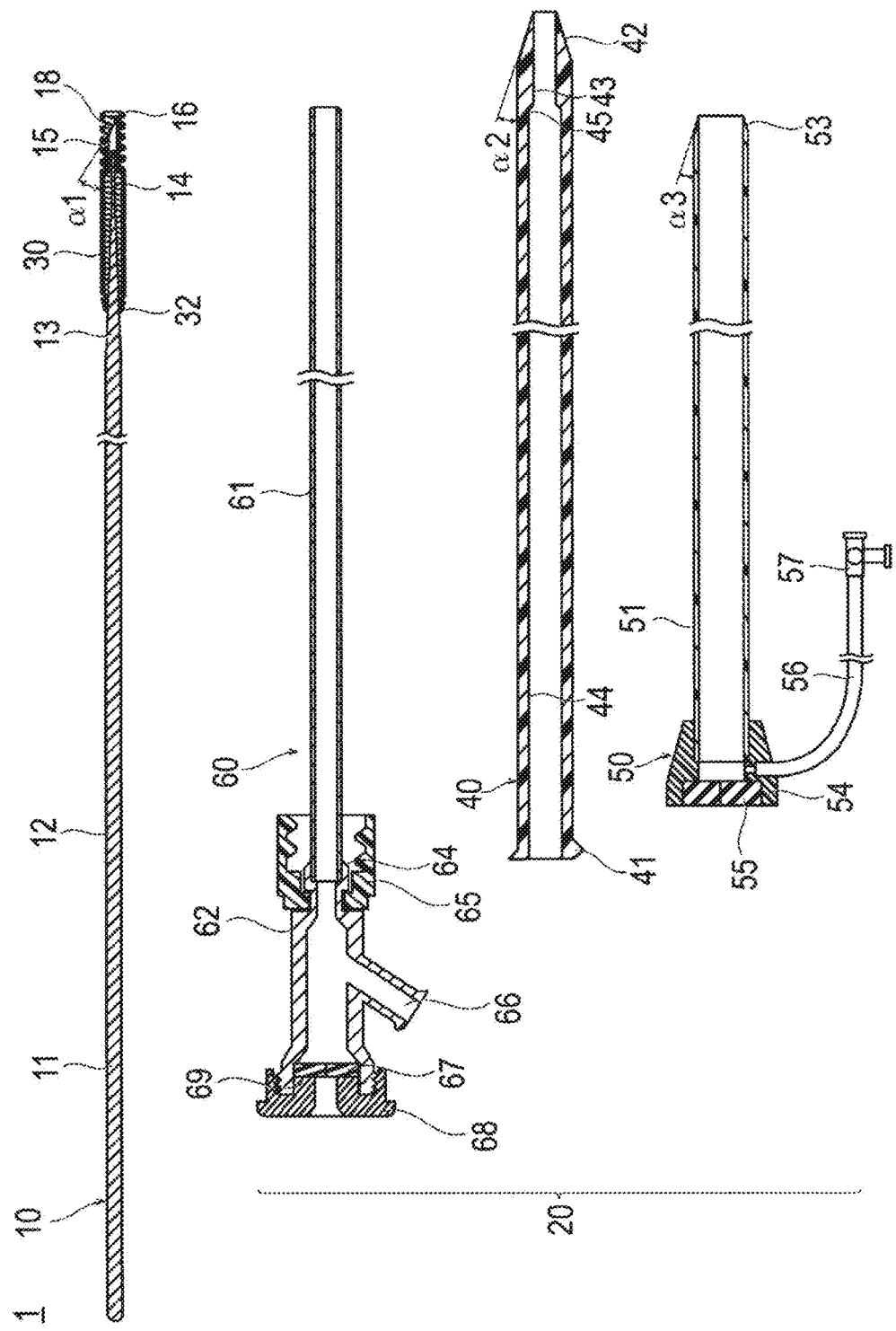
FIG. 2 is a sectional view illustrating the medical device according to the embodiment.
Figure 4:
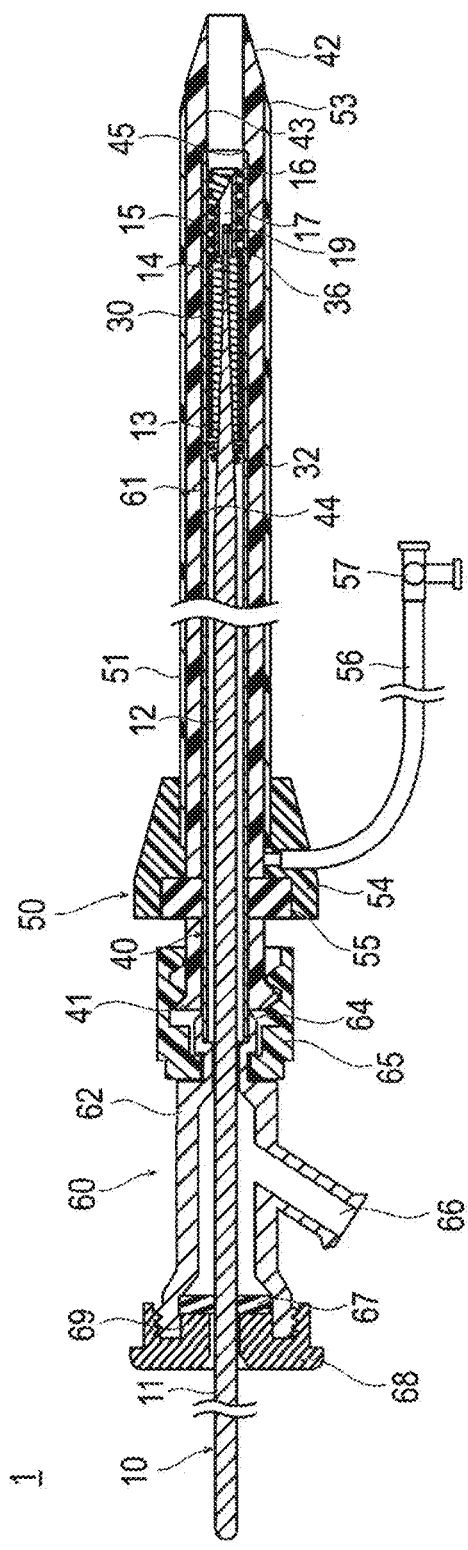
FIG. 4 is a sectional view illustrating a state where respective elements are assembled for the medical device according to the embodiment.

As illustrated in FIGS. 1, 2, and 4, the guide wire 10 can be inserted into the inserter 60, and the inserter 60 is inserted into the dilator 40. In order to properly puncture the fossa ovalis O, the medical device 1 needs to be provided with a suitable angle and rigidity so as to be properly oriented to the fossa ovalis O inside the right atrium R. The inserter 60 can be inserted into the dilator 40 so as to improve the rigidity and the angle of the medical device 1. For example, in a case of a known puncture needle, a metal shaft whose outer diameter is larger than the needle portion and which is bent at a predetermined angle is disposed on the proximal side of the sharp needle portion. According to the present embodiment, the inserter 60 is separately provided in order to provide the medical device 1 with the suitable angle and rigidity. The inserter 60 is independent of the guide wire 10. Accordingly, only the inserter 60 can be removed while leaving the guide wire 10 behind after the fossa ovalis O is punctured. Therefore, the outer sheath 50 can be more smoothly delivered via the guide wire 10. In addition, the inserter 60 is located in the dilator proximal portion 44 by bringing the inserter 60 into contact with the inner diameter decreasing portion 45 of the dilator 40. In this manner, the respective lumens of the inserter 60 and the dilator distal portion 43 are continuously formed with a substantially uniform inner diameter. Therefore, the guide wire 10 can be more freely inserted into the respective lumens of the inserter 60 and the dilator 40. Therefore, the guide wire 10 can be prevented from being caught on inside the dilator 40 having the inner diameter decreasing portion 45 for inserting the known puncture needle.

The inserter 60 has an insert main body 61 into which the guide wire 10 can be inserted, and an inserter hub 62 disposed on the proximal side of the insert main body 61.

The insert main body 61 is a tubular body into which the guide wire 10 can be inserted. An outer surface of the insert main body 61 may be coated with a low friction material so as to enable low friction contact with the dilator 40. For example, the low friction material includes fluorine-based polymer such as polytetrafluoroethylene (PTFE) and ethylene-tetrafluoroethylene copolymer (ETFE), or silicone oil. In addition, an inner surface of the insert main body 61 may be coated with the low friction material so as to enable low friction contact with the guide wire 10.

The distal portion of the insert main body 61 has an inserter bending portion 63 bent at a predetermined angle in a natural state. An angle $\beta 1$ of the inserter bending portion 63 with respect to the proximal portion of the insert main body 61 is not particularly restricted. For example, the angle $\beta 1$ may be 20 to 90 degrees, more preferably 30 to 85 degrees, and still more preferably 40 to 80 degrees. The inserter bending portion 63 has a role of causing the needle portion 16 of the guide wire 10 inserted into the right atrium to be directed toward the fossa ovalis O. An outer peripheral edge portion of the distal side end portion of the insert main body 61 is preferably subjected to surface processing so that the insert main body 61 can be smoothly inserted into the dilator 40.

The insert main body 61 is shorter than the dilator 40. The length of the insert main body 61 is appropriately set, and is 400 to 1,100 mm, for example. The outer diameter of the insert main body 61 is appropriately set, and is 0.5 to 1.5 mm, for example. The inner diameter of the insert main body 61 is appropriately set, and is 0.3 to 1.3 mm, for example. A radial clearance between the inner peripheral surface of the insert main body 61 and the outer peripheral surface of the needle portion 16 is appropriately set, and is 0.025 to 0.2 mm, for example.

A material for fabricating the insert main body 61 is preferably a flexible material. For example, it is possible to preferably use a shape memory alloy that exhibits a shape memory effect or super-elasticity when heated, metal such as stainless steel, tantalum, titanium, platinum, gold, and tungsten, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide. In addition, the insert main body 61 may contain the X-ray contrast material.

The inserter hub 62 has a cylinder portion 64 to be interlocked with the proximal portion of the insert main body 61, a first connection portion 65 to be connected to the dilator 40, a port portion 66, a valve body 67, and a rotation fixing portion 68. The cylinder portion 64 is located in an end portion on the distal side of the inserter hub 62. A lumen of the cylinder portion 64 can communicate with the lumen of the insert main body 61. The first connection portion 65 is a cylindrical member rotatably disposed on the outer peripheral surface of the cylinder portion 64. The inner peripheral surface of the first connection portion 65 has a female connector which can be screwed to the second connection portion 41 disposed in the proximal portion of the dilator 40. The port portion 66 enables, for example, a three-way stopcock or a syringe to be connected to the port portion 66. The port portion 66 enables priming to be performed on the lumen of the insert main body 61, or enables a contrast agent or a drug to be injected into the insert main body 61. In addition, the blood inside the living body can be guided outward by using the port portion 66 so as to measure blood pressure. The blood pressure is measured, thereby enabling an operator to accurately confirm whether the needle portion 16 reaches a desired position. A direction in which the port portion 66 is disposed for the inserter hub 62 coincides with a direction in which the inserter bending portion 63 is bent. In other words, the direction in which the inserter bending portion 63 is bent is the same direction in which the port portion 66 extends away from the hub 62. Therefore, by confirming the position of the port portion 66 on the inserter hub 62, the operator present outside the body is able to recognize (i.e., know) the direction in which the inserter bending portion 63 is bent. The valve body 67 is located inside the proximal portion of the inserter hub 62. The guide wire 10 slidably penetrates the valve body 67. The valve body 67 slidably comes into contact with the outer peripheral surface of the guide wire 10. For example, the valve body 67 is a member having a slit at the center of a disc-like elastic body. The elastic body may be made of, for example, natural rubber, silicone rubber, or various elastomers. The valve body 67 prevents blood from leaking out of the insert main body 61, and prevents air from being mixed into the body. The rotation fixing portion 68 is screwed to the outer peripheral surface of the inserter hub 62. The rotation fixing portion 68 is rotated relative to the outer peripheral surface of the inserter hub 62. In this manner, the rotation fixing portion 68 is movable in the axial direction. The rotation fixing portion 68 has a pressing portion 69 protruding to the distal side (axially projecting in the distal direction) so as to come into contact with the valve body 67. If the rotation fixing portion 68 is rotated and moved to the distal side, the pressing portion 69 presses the valve body 67, and compresses the valve body 67. In this manner, the valve body 67 can fix the guide wire 10 penetrating the valve body 67 so as to be immovable. In addition, if the rotation fixing portion 68 is rotated and moved to the proximal side, the pressing portion 69 moves in a direction away from the valve body 67. In this manner, the valve body 67 compressed by the pressing portion 69 is released, thereby enabling the guide wire 10 to slide on the valve body 67. While an inserted state of the guide wire 10 is maintained, the inserter 60 can inject the contrast agent or the drug from the port portion 66, or can measure the blood pressure. Therefore, the inserter 60 can be very conveniently used.

A material for fabricating the inserter hub 62 is not particularly restricted. However, for example, it is possible to preferably use a hard resin such as polycarbonate, polyethylene, polypropylene, and an ABS resin (generic term for acrylonitrile, butadiene, and styrene copolymer synthetic resin), or metal such as stainless steel.

The dilator 40 is used in order to widen or enlarge the hole of the fossa ovalis O which is formed by the guide wire 10. The distal side end portion of the dilator 40 has a tapered portion 42 whose diameter decreases in a tapered shape toward the distal side. The lumen in the dilator 40 is open at the end portion whose diameter decreases most in the tapered portion 42 (the distal-most end of the dilator 40). An inclination angle $\alpha 2$ with respect to the central axis of the tapered portion 42 is appropriately set. For example, the inclination angle $\alpha 2$ may be 1 to 20 degrees, more preferably 3 to 15 degrees, and still more preferably 4 to 10 degrees. The outer peripheral surface of the proximal portion of the dilator 40 has a second connection portion 41 which is configured to be interlocked with the first connection portion 65 of the inserter hub 62. The second connection portion 41 is a male connector.

The dilator 40 has a dilator distal portion 43 located on the distal side and having a relatively smaller inner diameter, and a dilator proximal portion 44 located on the proximal side and having a larger inner diameter than the dilator distal portion 43. An inner diameter decreasing portion 45 whose inner diameter decreases toward the distal side is disposed between the dilator distal portion 43 and the dilator proximal portion 44. The inner peripheral surface of the dilator proximal portion 44 can slidably come into close contact with the outer peripheral surface of the insert main body 61. In addition, the length of the dilator proximal portion 44 coincides with the length of the insert main body 61.

Therefore, if the insert main body 61 is inserted into the dilator proximal portion 44, the insert main body 61 is fixed to the dilator 40 at an accurate position. In this case, the distal side end portion of the insert main body 61 comes into contact with the inner diameter decreasing portion 45. The inner diameter of the dilator 40 may be constant along the axial direction.

The distal portion of the dilator 40 has a dilator bending portion 46 bent at a predetermined angle in a natural state (i.e., when no load/force is applied to the dilator 40). An angle $\beta 2$ of the dilator bending portion 46 with respect to the proximal portion of the dilator 40 is not particularly restricted. For example, the angle $\beta 2$ may be 10 to 70 degrees, more preferably 20 to 60 degrees, and still more preferably 30 to 50 degrees. The dilator bending portion 46 has a role of causing the puncture portion 15 of the guide wire 10 or the tapered portion 42 of the dilator 40 inserted into the right atrium to be directed toward the fossa ovalis O.

The length of the dilator 40 is appropriately set, and may be 150 to 1,500 mm, for example. The outer diameter of the dilator 40 is appropriately set, and may be 2 to 6 mm, for example. The inner diameter of the dilator distal portion 43 is appropriately set, and may be 0.5 to 1.5 mm, for example. The inner diameter of the dilator proximal portion 44 is appropriately set, and may be 1.0 to 2.0 mm, for example. The length of the dilator distal portion 43 is appropriately set. For example, the length may be 1 to 15 mm, more preferably 2 to 12 mm, and still more preferably 3 to 10 mm. The radial clearance between the inner peripheral surface of the dilator proximal portion 44 and the outer peripheral surface of the insert main body 61 is appropriately set, and may be 0.03 to 0.1 mm, for example.

A configuration material of the dilator 40 is preferably a flexible material. For example, it is possible to preferably use polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide, a shape memory alloy, or metal such as stainless steel, tantalum, titanium, platinum, gold, and tungsten. In addition, the dilator 40 may contain the X-ray contrast material or the ultrasound contrast material.

The outer sheath 50 provides an access route for the ablation catheter. The outer sheath 50 has a sheath main body 51, a hub 54 interlocked with the proximal portion of the sheath main body 51, a sheath port portion 56 communicating with the hub 54, and a valve body 55 disposed inside the hub 54.

The sheath main body 51 is an elongated tubular body which accommodates the dilator 40 so as to movable in the axial direction. The sheath main body 51 has the inner peripheral surface which smoothly slides with the dilator 40. The distal portion of the sheath main body 51 has a sheath bending portion 52 bent at a predetermined angle in a natural state. An angle $\beta 3$ of the sheath bending portion 52 with respect to the proximal portion of the sheath main body 51 is not particularly restricted. For example, the angle $\beta 3$ may be 10 to 180 degrees, more preferably 30 to 150 degrees, and still more preferably 45 to 135 degrees. The sheath bending portion 52 has a role of causing the puncture portion 15 of the guide wire 10 or the distal portion of the sheath main body 51 inserted into the right atrium to be directed toward the fossa ovalis O.

The distal side end portion of the sheath main body 51 has a sheath tapered portion 53 whose outer diameter decreases in a tapered shape toward the distal side. The lumen in the sheath main body 51 is open in an end portion whose diameter decreases most in the sheath tapered portion 53. That is, the lumen in the sheath main body 51 opens to the distal-most end of the sheath main body 51. An inclination angle α3 with respect to the central axis of the sheath tapered portion 53 is appropriately set. For example, the inclination angle α3 may be 1 to 15 degrees, more preferably 2 to 10 degrees, and still more preferably 3 to 7 degrees. In the sheath assembly 20 in which the dilator 40 is inserted into the outer sheath 50, the sheath tapered portion 53 can be located on the proximal side of the tapered portion 42 of the dilator 40 so as to be continuous with the tapered portion 42 (i.e., so that the sheath tapered portion 53 smoothly transitions to the tapered portion 42 of the dilator 40 as shown in FIG. 4). The inner peripheral surface of the sheath main body 51 preferably has a clearance from the outer peripheral surface of the dilator 40 so as to come into slidable contact with the outer peripheral surface of the dilator 40.

The dilator 40 can penetrate the sheath main body 51 along the entire length. Therefore, the length in the axial direction of the sheath main body 51 is shorter than that of the dilator 40.

The length of the sheath main body 51 is appropriately set, and may be 400 to 1,000 mm, for example. The outer diameter of the sheath main body 51 is appropriately set, and may be 2.5 to 7.0 mm, for example. The inner diameter of the sheath main body 51 is appropriately set, and may be 2 to 6 mm, for example. The radial clearance at the radius between the inner peripheral surface of the sheath main body 51 and the outer peripheral surface of the dilator 40 is appropriately set, and may be 0.1 to 0.5 mm, for example.

A material for fabricating the sheath main body 51 is preferably a flexible material. For example, it is possible to preferably use polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide. In addition, the configuration material of the sheath main body 51 may contain the X-ray contrast material, a metal blade, or a coil.

The hub 54 is disposed in the proximal portion of the sheath main body 51, and communicates with the lumen of the sheath main body 51. The dilator 40 penetrates the hub 54. The sheath port portion 56 is interlocked with the hub 54, and communicates with the lumen of the sheath main body 51 via the lumen of the hub 54. The end portion of the sheath port portion 56 has a three-way stopcock 57. A syringe is connected to the three-way stopcock 57. In this manner, priming can be performed on the lumen of the sheath main body 51, or the contrast agent or the drug can be injected into the sheath main body 51.

The valve body 55 is a member for sealing each lumen of the hub 54 and the sheath main body 51. The valve body 55 is flexibly deformable, and is located on the inner peripheral surface of the hub 54. The valve body 55 slidably comes into contact with the outer peripheral surface of the dilator 40. In addition, in a state where the dilator 40 is inserted into the valve body 55, the dilator 40 is pressed by an elastic force, and the valve body 55 can fix the dilator 40 and the outer sheath 50 to each other. Even if both of these are fixed by the valve body 55, the dilator 40 and the outer sheath 50 are gripped, and the force is applied thereto. In this manner, both of these can be relatively moved in the axial direction. In addition, the dilator 40 is pulled out of the hub 54. In this manner, the hole portion into which the dilator 40 of the valve body 55 is inserted is closed, and the lumen of the hub 54 is sealed from the proximal side. For example, the valve body 55 is a member having a slit at the center of a disc-like elastic body. For example, the elastic body is natural rubber, silicone rubber, or various elastomers. While the dilator 40 is allowed to be inserted and removed, the valve body 55 prevents blood from leaking out via the outer sheath 50, and prevents air from being mixed into the body.

In a state where the inserter 60, the dilator 40, and the outer sheath 50 are assembled, it is preferable that respective positions, bending directions, and bending angles of the inserter bending portion 63, the dilator bending portion 46, and the sheath bending portion 52 coincide or substantially coincide with each other. In this manner, the needle portion 16 of the guide wire 10 can be caused to protrude in a desired direction.

Figure 5:
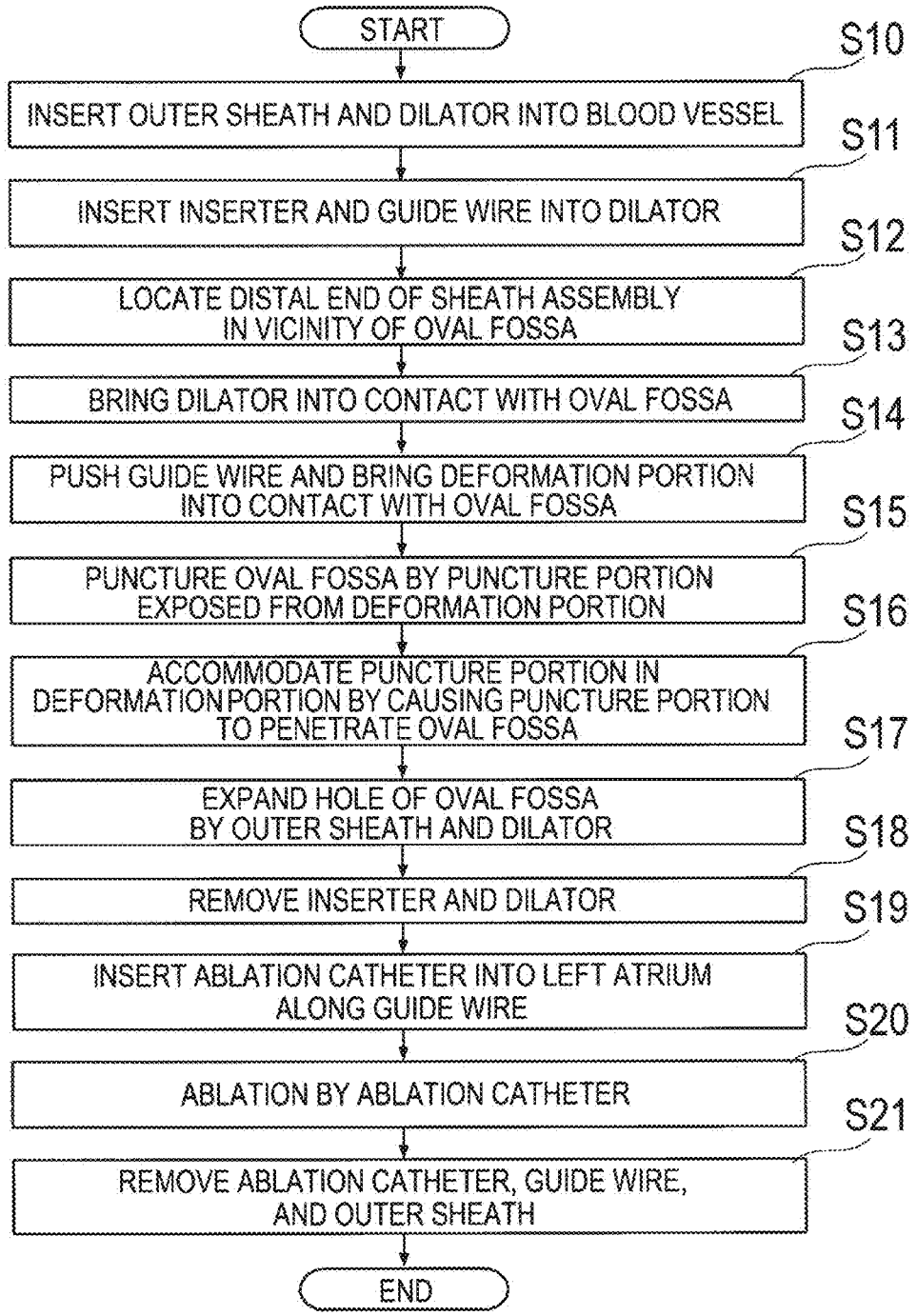
FIG. 5 is a flowchart for describing a medical procedure using the medical device.

Next, a method of providing an access route for the ablation catheter by using the medical device 1 according to the present embodiment so as to open the hole in the fossa ovalis O will be described with reference to a flowchart illustrated in FIG. 5.

First, a femoral vein is punctured using a needle, and a general-purpose guide wire (not illustrated) is inserted into the needle. Next, the needle is removed, and along the general-purpose guide wire, an assembly in which the dilator 40 is inserted into or positioned inside of the outer sheath 50 is inserted into the blood vessel (Step S10). The assembly is pushed forward while the general-purpose guide wire is moved ahead. The assembly reaches beyond the right atrium R, and the distal end of the dilator 40 reaches a superior vena cava. Thereafter, the general-purpose guide wire is removed. Instead of the general-purpose guide wire, the guide wire 10 may be used.

Figure 6:
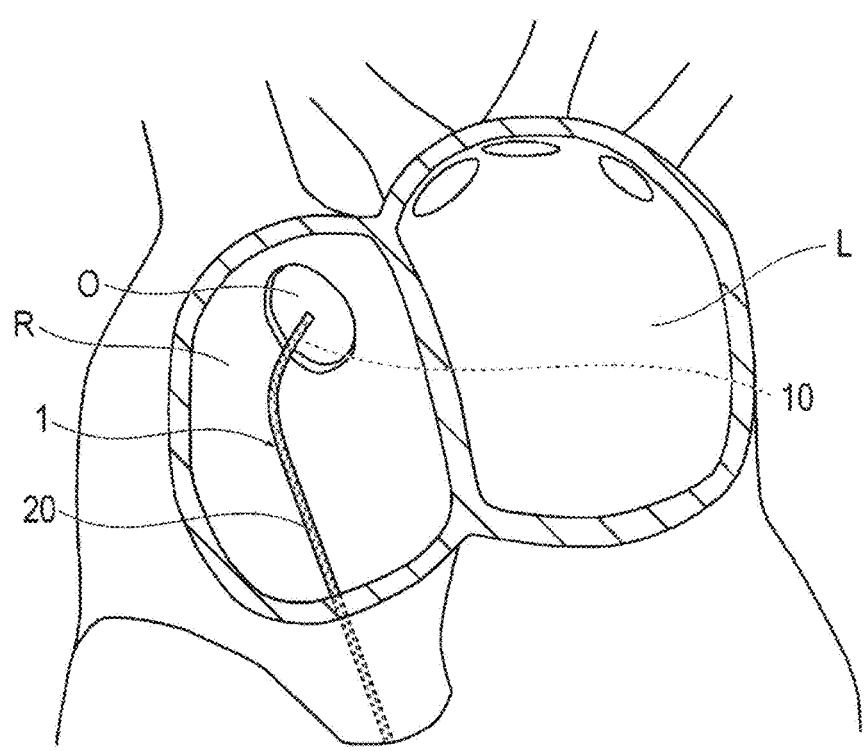
FIG. 6 is a partial sectional view internally illustrating a heart.
Figure 7A:
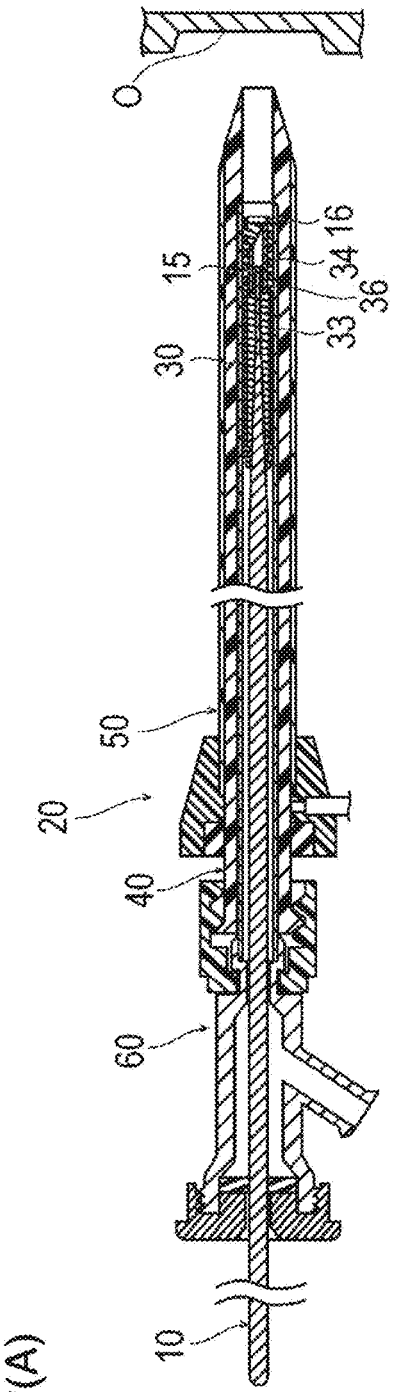
FIGS. 7(A) and 7(B) are sectional views illustrating a state when puncture is performed by the medical device.

Next, the inserter 60 and the guide wire 10 are inserted into the assembly defined by the outer sheath 50 and the dilator 40 (Step S11) (refer to FIG. 4). In this case, the opening portion on the distal side of the dilator 40 and the opening portion on the distal side of the inserter 60 are both positioned distal of the distal end of the guide wire 10. The first connection portion 65 of the inserter 60 is interlocked with the second connection portion 41 of the dilator 40. The inserter 60 may not be interlocked with the dilator 40. Therefore, the first connection portion 65 and the second connection portion 41 may not be provided. In the guide wire 10, the outer peripheral surface of the deformation portion 30 accommodating the puncture portion 15 is not completely constrained. Therefore, when the guide wire 10 moves inside the inserter 60 and the dilator 40, the puncture portion 15 of the guide wire 10 maintains a state of being accommodated in the deformation portion 30. Next, the sheath assembly 20 (the sheath 50, the dilator 40 and the inserter 60) is moved rearward, and is pulled into the right atrium R. That is, the sheath assembly is first moved forward and is pushed into the Superior Vena Cava positioned above the right atrium via the right atrium. The sheath assembly is then moved rearwardly and pulled into the right atrium. In this manner, as illustrated in FIGS. 6 and 7(A), the distal side end portion of the sheath assembly 20 is naturally guided to the vicinity of the fossa ovalis O (Step S12).

Figure 7B:
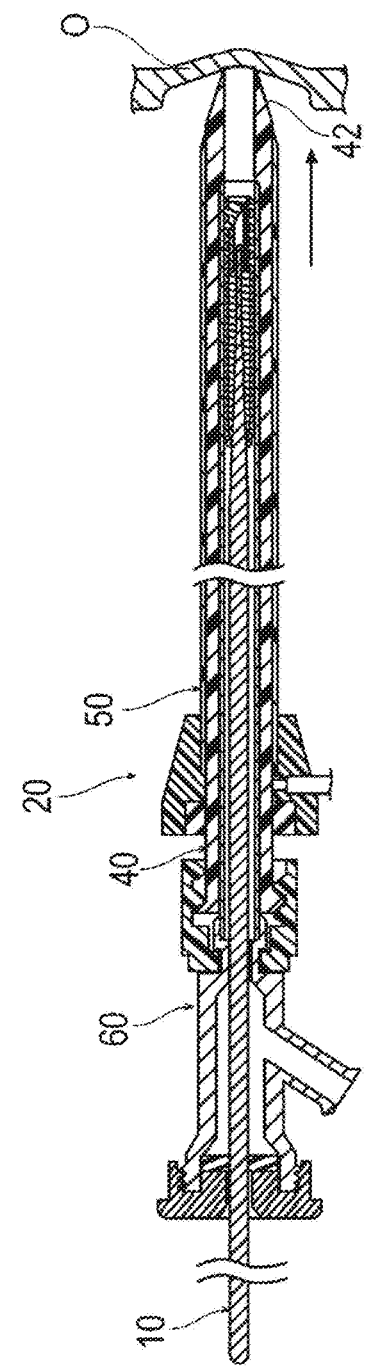

Next, while the left atrium L and the right atrium R are observed using an intra cardiac echo catheter (ICE), the sheath assembly 20 is pushed into the distal side of the fossa ovalis O as illustrated in FIG. 7(B) (Step S13). In this manner, the fossa ovalis O is pressed, and is brought into a state of protruding toward the left atrium L side by the dilator 40. In this case, the distal portion of each of the outer sheath 50, the dilator 40, and the inserter 60 is bent. Accordingly, the end portion on the distal side of the dilator 40 can be easily directed to the fossa ovalis O. The fossa ovalis O may not be brought into the state of protruding toward the left atrium L side. The medical device 1 is reinforced by the inserter 60 inserted into the dilator 40. Therefore, even if the known puncture needle which is highly rigid and bent is not inserted, the medical device 1 can be directed to the fossa ovalis O by using the rigidity and angle which are suitable for puncture.

Next, as illustrated in FIG. 8(A), the proximal portion of the guide wire 10 located outside the body is pushed forward in the inserter hub 62. In this manner, the guide wire 10 moves to the distal side or in the distal direction, and the deformation portion 30 located in the distal end of the guide wire 10 comes into contact with the fossa ovalis O (Step S14). In this manner, the force acting toward the proximal side is applied to the distal end of the deformation portion 30 located in the most distal portion of the guide wire 10. In a case where the end portion on the distal side of the deformation portion 30 comes into contact with the fossa ovalis O in the same plane, the needle portion 16 is perpendicular to the fossa ovalis O. In this manner, the deformation portion 30 is likely to shrink, the needle portion 16 is likely to be exposed, and the needle portion 16 is likely to puncture the fossa ovalis O. For example, in a case where the deformation portion 30 is a cylinder, if the entire circumference of the end portion on the distal side comes into contact with the fossa ovalis O at the same time, the fossa ovalis O is likely to be punctured. The deformation portion 30 is accommodated inside the inserter 60 and the dilator 40, and thus, the deflection is restricted. Therefore, the distal end of the sparse pitch portion 34 of the deformation portion 30 receives the force acting toward the proximal side. In this manner, the sparse pitch portion 34 of the deformation portion 30 elastically shrinks in the axial direction so as to decrease the gap between the adjacent windings of the wire rod 31. The deformation portion 30 surrounds the shaft diameter decreasing portion 13 having lowered rigidity due to the decreased outer diameter, and the shaft distal portion 14 on the distal side from the shaft diameter decreasing portion 13. Therefore, the deformation portion 30 decreases the gap surrounding the shaft portion by compensating for the periphery of the shaft portion 11 which is otherwise likely to be deflected due to the lowered rigidity, and prevents the shaft portion 11 from being deflected inside the dilator 40 or the inserter 60. Therefore, the deformation portion 30 prevents the movement of the guide wire 10 in the axial direction inside the dilator 40 and the inserter 60 from being absorbed by the shaft portion 11 which is likely to be deflected. Therefore, the fossa ovalis O can be effectively punctured by the puncture portion 15 fixed to the shaft portion 11. In addition, the dense pitch portion 33 cannot shrink in the axial direction. Accordingly, the dense pitch portion 33 is accommodated inside the dilator 40 or the inserter 60, and the deflection is restricted. In this manner, the force can be effectively transmitted in the axial direction, thereby enabling effective puncture.

If the deformation portion 30 shrinks in the axial direction by coming into contact with the fossa ovalis O, the needle portion 16 of the puncture portion 15 accommodated in the deformation portion 30 is exposed. Therefore, if the guide wire 10 is pushed into the distal side of the fossa ovalis, a hole can be formed in the fossa ovalis O by the puncture portion 15 exposed from the deformation portion 30 (Step S15). It is desirable that a force which causes the deformation portion 30 to shrink in the axial direction until the needle portion 16 is exposed is greater than a value of frictional resistance acting on the guide wire 10 when the guide wire 10 is inserted into the dilator 40 or the living body. In this manner, when the guide wire 10 moves inside the dilator 40 or the living body, the needle portion 16 can be prevented from protruding since the deformation portion 30 shrinks due to the friction force. If the guide wire 10 is further pushed in the distal direction or toward the distal side after the puncture portion 15 reaches the left atrium L through the fossa ovalis O, the deformation portion 30 penetrates the formed hole. If the distal end of the deformation portion 30 penetrates the hole, or if the second fixing portion 36 fixed to the puncture portion 15 of the deformation portion 30 penetrates the hole, as illustrated in FIG. 8(B), the elastically shrunk deformation portion 30 stretches in the axial direction due to a self-restorative force. In this manner, the puncture portion 15 is one again accommodated in (covered by) the deformation portion 30 (Step S16). The deformation portion 30 accommodating the puncture portion 15 protrudes from the dilator 40. Accordingly, the deflection of the deformation portion 30 is not restricted, and the deformation portion 30 can be freely deflected. Therefore, the puncture portion 15 inside the left atrium L maintains a state of being accommodated in the deformation portion 30. Therefore, the puncture portion 15 can be prevented from erroneously puncturing an unintended position. In the guide wire 10, the deformation portion 30 is disposed in the outer periphery of the thin shaft portion 11. Therefore, the deformation portion 30 is pushed into the hole formed by the needle portion 16, thereby enabling the hole to be widened. Therefore, the guide wire 10 can form the hole having a proper size in the fossa ovalis O by using the deformation portion 30. In a case where only a portion of the puncture portion 15 protrudes from the dilator 40, the puncture portion 15 is supported by the dilator 40, thereby enabling the puncture portion 15 to show puncture ability. Therefore, in order to ensure safety, after the needle portion 16 penetrates the fossa ovalis O, it is preferable that the distal end of the deformation portion 30 is located on the distal side from the puncture portion 15. Thereafter, if the whole puncture portion 15 protrudes from the dilator 40, the puncture portion 15 is no longer supported by the dilator 40. In this manner, a portion of the guide wire 10 which protrudes from the dilator 40 is flexibly bent. Accordingly, the puncture portion 15 does not show the puncture ability, and the safety can be ensured.

If the puncture portion 15 penetrates the fossa ovalis O, a portion of the tapered portion 42 of the dilator 40 pressing the fossa ovalis O against the left atrium L side enters the hole open in the fossa ovalis O. The portion of the tapered portion 42 may not enter the hole of the fossa ovalis O.

If the puncture portion 15 penetrates the fossa ovalis O, the left atrium L satisfactorily communicates with the lumen of the dilator 40 and the inserter 60 via the through-hole 17 of the puncture portion 15, the gap between the deformation portion 30 and the shaft portion 11, and the gap between the windings of the wire rod 31 of the proximal diameter decreasing portion 35. Therefore, the blood pressure is measured via the port portion 66 of the inserter 60. In this manner, it is possible to accurately confirm whether the puncture portion 15 reaches the left atrium L. In addition, the contrast agent can be released to the left atrium L from the port portion 66 of the inserter 60 via the through-hole 17 of the puncture portion 15.

Next, the medical device 1 is moved to the distal side or in the distal (forward) direction while the guide wire 10 is moved ahead. In this manner, as illustrated in FIG. 9(A), the tapered portion 42 of the dilator 40 and the sheath tapered portion 53 of the outer sheath 50 pass through the fossa ovalis O while widening the hole of the fossa ovalis O, and reach the left atrium L. In this case, the respective diameters of the tapered portion 42 and the sheath tapered portion 53 are decreased to the distal side. Accordingly, the hole of the fossa ovalis O can be smoothly widened (Step S17). In addition, the guide wire 10 maintains a state of penetrating the fossa ovalis O. Accordingly, the dilator 40 and the outer sheath 50 can be easily pushed into the hole of the fossa ovalis O along the guide wire 10. In addition, when the fossa ovalis O is punctured by the puncture portion 15, a portion of the tapered portion 42 of the dilator 40 enters the hole of the fossa ovalis O. Accordingly, the dilator 40 and the outer sheath 50 are easily pushed into the hole of the fossa ovalis O. In addition, the guide wire 10 is moved ahead. In this manner, the medical device 1 can be safely moved to a left atrial wall side (for example, the vicinity of the pulmonary vein).

Next, as illustrated in FIG. 9(B), the outer sheath 50 and the guide wire 10 are left behind (i.e., are generally maintained in the position shown in FIG. 9A), and the inserter 60 and the dilator 40 are moved in the proximal direction and are removed from the body (Step S18). The hole of the fossa ovalis O which is widened by the dilator 40 is maintained by the outer sheath 50. If the dilator 40 is removed from the outer sheath 50, the valve body 55 is closed. Accordingly, blood can be prevented from leaking out, and air can be prevented from being mixed into the blood vessel. Thereafter, the ablation catheter is inserted along the guide wire 10 via the valve body 55 from the proximal side or proximal end of the outer sheath 50. In this manner, the ablation catheter can be inserted into the left atrium L by using the outer sheath 50 penetrating the fossa ovalis O (Step S19). After the ablation is performed on the left atrium L by the ablation catheter (Step S20), if the ablation catheter, the guide wire 10, and the outer sheath 50 are removed from the body (Step S21), the hole of the fossa ovalis O is narrowed. In this manner, the medical procedure is completed.

As described above, according to the first embodiment, there is provided the guide wire 10 for guiding the tubular elongated body (for example, the dilator 40) to be inserted into the living body. The guide wire 10 includes the flexible and elongated shaft portion 11, the puncture portion 15 located in the distal portion of the shaft portion 11, and whose distal side includes the needle portion 16 for forming the hole in the biological tissue, and the deformable deformation portion 30 fixed to the shaft portion 11 or the puncture portion 15. The deformation portion 30 located inside the dilator 40 restricts the deflection of the distal portion of the shaft portion 11.

According to the guide wire 10 configured as described above, in a state where the deformation portion 30 is located inside the dilator 40, the dilator 40 and the deformation portion 30 restrict the deflection of the distal portion of the shaft portion 11. In this manner, the puncture portion 15 can form the hole in the biological tissue (for example, the fossa ovalis O). In this way, the guide wire 10 can form the hole in the biological tissue while functioning as the guide wire 10 for guiding the dilator 40 or the ablation catheter. Then, since the guide wire 10 does not need a separate device having the puncture function, the guide wire 10 shows satisfactory workability. In addition, the guide wire 10 can ensure the safety by preventing the puncture needle portion 16 from performing erroneous puncture.

In addition, the force acting toward the proximal side is received by the distal end of the deformation portion 30. Accordingly, in a state where the deformation portion 30 is accommodated inside the dilator 40, the deflection of the distal portion of the shaft portion 11 is restricted by the deformation portion 30. In a state where the deformation portion 30 is located outside the dilator 40, the distal portion of the shaft portion 11 is deflected together with the deformation portion 30. In this way, in a state where the deformation portion 30 is exposed outward of the dilator 40, the force acting toward the proximal side is received by the distal end of the deformation portion 30. In this manner, the deformation portion 30 and the distal portion of the shaft portion 11 are deflected. Therefore, after penetrating the biological tissue (for example, the fossa ovalis O), the needle portion 16 does not puncture other biological tissue. Accordingly, while the safety is maintained, the dilator 40 can be guided to a desired position. In addition, in a state where the deformation portion 30 is accommodated in the dilator 40, the deflection of the distal portion of the shaft portion 11 is restricted by the dilator 40 and the deformation portion 30. In this manner, the puncture portion 15 can form the hole in the biological tissue (for example, the fossa ovalis O).

In addition, the deformation portion 30 is a member for accommodating the puncture portion 15. In a state where the deformation portion 30 is accommodated inside the dilator 40, the distal end receives the force acting toward the proximal side. The deformation portion 30 elastically shrinks in the axial direction so as to expose the needle portion 16. In a state where the deformation portion 30 is located outside the dilator 40, the distal end of the deformation portion 30 receives the force acting toward the proximal side, and the deformation portion 30 is deflected together with the distal portion of the shaft portion 11, thereby maintaining a state of accommodating the needle portion 16. Therefore, in the guide wire 10, in a state where the deformation portion 30 is exposed outward of the dilator 40, even if the distal end of the deformation portion 30 receives the force acting toward the proximal side, the deformation portion 30 is deflected, thereby maintaining a state where the needle portion 16 is accommodated in the deformation portion 30. Therefore, in the guide wire 10, the needle portion 16 does not protrude from the deformation portion 30. While the safety is maintained, the guide wire 10 can guide the dilator 40 to a desired position. In addition, in a state where the deformation portion 30 is accommodated in the dilator 40, the distal end of the deformation portion 30 receives the force acting toward the proximal side by coming into contact with the biological tissue. In this manner, the deformation portion 30 elastically shrinks in the axial direction so as to expose the puncture portion 15. Therefore, since the deformation portion 30 is accommodated in the dilator 40, the hole can be formed in the biological tissue by the puncture portion 15. After the protruding puncture portion 15 penetrates the biological tissue, the deformation portion 30 restores its own original shape by the self-restorative force, and accommodates the puncture portion 15. In addition, in the guide wire 10, the hole formed by the needle portion 16 can be widened by the deformation portion 30 accommodating the needle portion 16, and the hole having a proper size can be formed in the biological tissue.

In addition, the deformation portion 30 is a tubular member for accommodating the puncture portion 15. In this manner, the deformation portion 30 can satisfactorily accommodate the puncture portion 15. The deformation portion may not have the tubular shape as long as the deformation portion can restrict the deflection of the shaft portion 11 inside the tubular body such as the dilator 40 and can be deflected in synchronization with the shaft portion 11.

In addition, the deformation portion 30 is elastically deformable. In this manner, in a state of accommodating the needle portion 16, the deformation portion 30 is elastically deformed so that the needle portion 16 protrudes. Thereafter, the deformation portion 30 can be restored to its original shape so as to accommodate the needle portion 16. The deformation portion may not be elastically deformed as long as the deformation portion can restrict the deflection of the shaft portion 11 inside the tubular body such as the dilator 40 and can be deflected in synchronization with the shaft portion 11. For example, the deformation may be plastically deformed.

In addition, the puncture portion 15 has the through-hole 17 penetrating in the axial direction. In this manner, if the puncture portion 15 penetrates the biological tissue (for example, the fossa ovalis O), for example, the contrast agent can be supplied into the living body via the puncture portion 15. In addition, if the puncture portion 15 penetrates the biological tissue, the pressure inside the living body can be measured via the through-hole 17, and it is possible to accurately recognize whether or not the puncture portion 15 penetrates the biological tissue.

In addition, the deformation portion 30 is a spiral member, and has the gap between the spiral windings of the wire rod 31 aligned with each other in the axial direction. In this manner, in a state of covering the needle portion 16 of the puncture portion 15, the deformation portion 30 can shrink in the axial direction so as to decrease the gap between axially adjacent windings of the wire rod 31, and can expose the needle portion 16.

In addition, the deformation portion 30 has the sparse pitch portion 34 having the gap between the spiral windings of the wire rod 31 aligned with each other in the axial direction, and the dense pitch portion 33 located on the proximal side from the sparse pitch portion 34, and in which the inter-pitch distance between the spiral windings of the wire rod 31 aligned with each other in the axial direction is shorter than that of the sparse pitch portion 34. In this manner, in a state of covering the needle portion 16, the sparse pitch portion 34 can shrink in the axial direction so as to decrease the gap between the axially adjacent windings of the wire rod 31, and can expose the needle portion 16. In addition, the dense pitch portion 33 is less likely to shrink in the axial direction. Accordingly, the force is effectively transmitted in the axial direction, thereby enabling effective puncture.

In addition, the distal end of the deformation portion 30 receives the force acting toward the proximal side. In this manner, the inter-pitch distance of the spiral of the deformation portion 30 is shortened so as to restrict the deflection of the distal portion of the shaft portion 11. That is, if the inter-pitch distance of the spiral of the deformation portion 30 is shortened, when the distal portion of the shaft portion 11 is deflected, the spiral windings of the wire rod 31 aligned with each other in the axial direction come into contact and interfere with each other. Accordingly, the deformation portion 30 is less likely to be deformed, thereby restricting the deflection of the shaft portion 11. Therefore, the force can be effectively transmitted in the axial direction by the shaft portion 11, thereby enabling the effective puncture.

In addition, the deformation portion 30 has the first fixing portion 32 fixed to the shaft portion 11, and the second fixing portion 36 fixed to the proximal side portion from the needle portion 16 of the puncture portion 15, on the distal side from the first fixing portion 32 and on the proximal side from the distal end of the deformation portion 30. In this manner, the distal side portion from the second fixing portion 36 of the deformation portion 30 can accommodate the puncture portion 15 so that the puncture portion 15 can protrude therefrom. Furthermore, the portion between the second fixing portion 36 and the first fixing portion 32 of the deformation portion 30 can effectively transmit the force in the axial direction by reinforcing the shaft portion 11, thereby enabling the effective puncture. The first fixing portion 32 and the second fixing portion 36 may be formed of a material which is melted by soldering, bonding, or welding.

In addition, the shaft portion 11 has the shaft diameter decreasing portion 13 whose outer diameter decreases in a tapered shape toward the distal side. The deformation portion 30 is located in the outer periphery of at least the shaft diameter decreasing portion 13 of the shaft portion 11. In this manner, the deformation portion 30 can surround the shaft diameter decreasing portion 13 having lowered rigidity due to the decreased outer diameter, and the distal side from the shaft diameter decreasing portion 13 of the shaft portion 11. Therefore, the deformation portion 30 decreases the gap by compensating for the periphery of the shaft portion 11 which is likely to be deflected due to the lowered rigidity, and prevents the shaft portion 11 from being deflected inside the elongated body such as the dilator 40. Therefore, the movement of the guide wire 10 in the axial direction inside the dilator 40 is prevented from being absorbed by the shaft portion 11 which is likely to be deflected, and the biological tissue can be effectively punctured by the puncture portion 15 fixed to the shaft portion 11. The deformation portion 30 may be fixed to the shaft proximal portion 12 on the proximal side from the shaft diameter decreasing portion 13.

In addition, the deformation portion 30 is fixed to the shaft diameter decreasing portion 13 whose outer diameter further decreases than the shaft proximal portion 12. In this manner, the guide wire 10 can be prevented from having excessively strong rigidity.

In addition, the distal side end surface of the deformation portion 30 is inclined in a tapered shape so that the inner side in the radial direction protrudes to the distal side. In this manner, the deformation portion 30 can smoothly pass through the hole formed in the biological tissue with less resistance.

In addition, according to the present embodiment, there is provided the guide wire 10 for guiding the tubular elongated body (for example, the dilator 40) to be inserted into the living body. The guide wire 10 includes the flexible and elongated shaft portion 11, the puncture portion 15 located in the distal portion of the shaft portion 11 so as to form the hole in the biological tissue, and the deformable deformation portion 30 fixed to the shaft portion 11. In a state where the deformation portion 30 is located outside the dilator 40, the distal end of the deformation portion 30 receives the force acting toward the proximal side, and the deformation portion is deflected together with the distal portion of the shaft portion 11 so as to maintain a state of accommodating the puncture portion 15.

In the guide wire 10 configured as described above, in a state where the deformation portion 30 is located inside the dilator 40, the dilator 40 and the deformation portion 30 restrict the deflection of the distal portion of the shaft portion 11. In this manner, the puncture portion 15 can form the hole in the biological tissue (for example, the fossa ovalis O). In this way, the guide wire 10 can form the hole in the biological tissue while functioning as the guide wire 10 for guiding the dilator 40 or the ablation catheter. Then, since the guide wire 10 does not need a separate device having the puncture function, the guide wire 10 shows satisfactory workability. In addition, in a state where the deformation portion 30 is located outside the elongated body such as the dilator 40, a state of accommodating the puncture portion 15 is maintained. Accordingly, improved safety can be achieved by preventing the puncture portion 15 from performing erroneous puncture.

In addition, according to the first embodiment, there is provided the guide wire 10 for guiding the tubular dilator 40 to be inserted into the living body. The guide wire 10 has the flexible and elongated shaft portion 11, the puncture portion 15 located in the distal portion of the shaft portion 11 so as to form the hole in the biological tissue, and the stretchable cover portion (for example, the deformation portion 30) that covers the puncture portion 15. If the cover portion is exposed from the dilator 40, the cover portion covers the puncture portion 15. Therefore, the guide wire 10 is covered by the stretchable cover portion after the puncture portion 15 forms the hole in the biological tissue. Therefore, the guide wire 10 can ensure the safety by preventing the puncture portion 15 from performing the erroneous puncture.

In addition, according to the first embodiment, there is provided the medical device 1 for forming the hole in the biological tissue (for example, the fossa ovalis O) inside the living body. The medical device 1 includes the tubular elongated body (for example, the dilator 40) to be inserted into the living body, and the guide wire 10 insertable into the dilator 40. The guide wire 10 has the flexible and elongated shaft portion 11, the puncture portion 15 located in the distal portion of the shaft portion 11, and whose distal side includes the needle portion 16 for forming the hole in the biological tissue, and the deformable deformation portion 30 fixed to the shaft portion 11 or the puncture portion 15. The deformation portion 30 located inside the dilator 40 restricts the deflection of the distal portion of the shaft portion 11.

The medical device 1 configured as described above has the dilator 40 into which the above-described guide wire 10 is inserted. Accordingly, the deformation portion 30 of the guide wire 10 can be accommodated in the dilator 40. In a state where the deformation portion 30 is accommodated in the dilator 40, the dilator 40 and the deformation portion 30 restrict the deflection of the distal portion of the shaft portion 11. In this manner, the puncture portion 15 can form the hole in the biological tissue. In addition, in a state where the deformation portion 30 is exposed outward of the dilator 40, the distal end of the deformation portion 30 receives the force acting toward the proximal side. In this manner, the deformation portion 30 and the distal portion of the shaft portion 11 are deflected. Therefore, in the medical device 1, after penetrating the biological tissue (for example, the fossa ovalis O), the needle portion 16 does not puncture other biological tissue. Accordingly, while the safety is maintained, the dilator 40 can be guided to a desired position by the guide wire 10.

In addition, another aspect of the disclosure here includes the treatment method (for example, a medical treatment method) for forming the hole in the biological tissue (for example, the fossa ovalis O) inside the living body by using the above-described medical device 1. The treatment method has Step S13 of accommodating the needle portion 16 and the deformation portion 30 of the guide wire 10 in the elongated body (for example, the dilator 40), and bringing the distal end of the dilator 40 into contact with the biological tissue, and Step S15 of moving the guide wire 10 to the distal side with respect to the dilator 40, pressing the distal end of the deformation portion 30 against the biological tissue, and causing the needle portion 16 to form the hole in the biological tissue, and Step S17 of moving the dilator 40 along the guide wire 10.

According to the treatment method implemented as described above, the needle portion 16 and the deformation portion 30 of the guide wire 10 are accommodated in the dilator 40. The distal end of the deformation portion 30 is pressed against the biological tissue. The hole is formed in the biological tissue by the needle portion 16. Therefore, since the treatment method does not need a separate device having the puncture function, the treatment method shows satisfactory workability. In addition, in a state where the deformation portion 30 is located outside the dilator 40, the distal end of the deformation portion 30 receives the force acting toward the proximal side. In this manner, the distal portion of the shaft portion 11 is deflected together with the deformation portion 30. Therefore, the treatment method can ensure the safety by preventing the puncture needle portion 16 from performing erroneous puncture. In addition, according to the treatment method, the hole formed by the needle portion 16 can be widened by the deformation portion 30 accommodating the needle portion 16, and the hole having a proper size can be formed in the biological tissue.

In addition, another aspect of the treatment method includes Step S13 of accommodating the puncture portion 15 and the cover portion (for example, the deformation portion 30) of the guide wire 10 in the elongated body (for example, the dilator 40), and bringing the distal end of the elongated body into contact with the biological tissue, Step S15 of moving the guide wire 10 to the distal side with respect to the elongated body, pressing the distal end of the cover portion against the biological tissue so that the cover portion shrinks in the axial direction, and forming the hole in the biological tissue by the puncture portion 15 exposed from the cover portion, Step S16 of pushing the cover portion into the hole of the biological tissue subsequently to the puncture portion 15 so that the cover portion covers the puncture portion covering the puncture portion 15, and Step S17 of moving the elongated body along the guide wire 10. Therefore, since the treatment method does not need a separate device having the puncture function, the treatment method shows satisfactory workability. In addition, according to the treatment method, the cover portion covers the puncture portion 15 which forms the hole in the biological tissue. Accordingly, the safety can be ensured by preventing the puncture portion 15 from performing erroneous puncture. In addition, according to the treatment method, the hole formed by the puncture portion 15 can be widened by the cover portion accommodating the puncture portion 15, and the hole having a proper size can be formed in the biological tissue. Then, the elongated body is moved along the guide wire 10. In this manner, for example, the elongated body serving as the dilator 40 can be moved from one atrium to the other atrium.

The present invention is not limited to the above-described embodiment, and can be modified in various ways by those skilled in the art within the technical concept of the present invention. For example, the above-described medical device may be used in order to puncture the biological tissue inside the living body other than the fossa ovalis. In addition, the medical device may not be used in order to widen the hole in the biological tissue. For example, the medical device may be used as an injection tool for puncturing the biological tissue (for example, a myocardium or an organ) inside the living body so as to inject a drug, a contrast agent, or physiological salt solution. For example, the drug may contain cells to be injected into the myocardium. The elongated body accommodating the needle portion 16 may be pushed into or may not be pushed into the hole formed in the biological tissue.

In addition, the deformation portion 30 may be formed using a plurality of the wire rods instead of one wire rod 31. Therefore, the deformation portion may be formed using a multi-row spring or a mesh. In addition, the deformation portion may be a flexible resin tube.

In addition, the dilator 40 and the inserter 60 are separate from each other, but may be integrated with each other. In addition, if the dilator 40 is provided, the inserter 60 may not be provided.

In addition, as in a first modification example illustrated in FIG. 10(A), a dense pitch portion 72 of a deformation portion 71 may extend to a proximal portion of a guide wire 70. Then, the shaft portion 11 and the deformation portion 71 are not fixed to each other. In the description below, features that are the same or similar to those described above are identified by the same reference numerals and a detailed description of such features is not repeated. The axial center of the spiral of the deformation portion 71 may coincide with the axial center of the shaft diameter decreasing portion 13 and the shaft distal portion 14, but may be biased in any direction of the circumferential direction. A direction in which the axial center of the spiral of the deformation portion 71 is biased with respect to the axial center of the shaft diameter decreasing portion 13 and the shaft distal portion 14 is not particularly limited. However, for example, the direction is oriented to a side having the needle fixing portion 19, or a side opposite thereto. In this manner, a bending direction of the guide wire 70 (to be described later) is likely to be designated. The proximal portion of the dense pitch portion 72 can be operated together with the shaft portion 11 on the operator's hand side. If the proximal portion of the dense pitch portion 72 is moved to the proximal side with respect to the shaft portion 11, as illustrated in FIG. 10(B), the puncture portion 15 fixed to the deformation portion 71 by the second fixing portion 36 receives the force acting toward the proximal side. Then, the puncture portion 15 is fixed to the shaft portion 11 by the needle fixing portion 19 located at one position in the circumferential direction of the inner peripheral surface. Therefore, if the puncture portion 15 receives force acting toward the proximal side, the shaft portion 11 can be pulled and inclined to the side having the needle fixing portion 19 in the circumferential direction. In this manner, the shaft portion 11 and the deformation portion 71 are operated on the operator's hand side, thereby enabling the guide wire 70 to be directed in a desired direction. Therefore, the guide wire 70 can select the blood vessel into which the guide wire 70 is inserted.

In addition, as in a second modification example illustrated in FIG. 11(A), a deformation portion 81 may have a dense pitch portion 82 extending to a proximal portion of a guide wire 80, and a second sparse pitch portion 83 located on the proximal side of the dense pitch portion 82. The second sparse pitch portion 83 has a gap between the axially adjacent windings of the wire aligned with each other in the axial direction. The shaft portion 11 and the deformation portion 81 are not fixed to each other. If the proximal end of the deformation portion 81 is moved to the distal side with respect to the shaft portion 11, as illustrated in FIG. 11(B), the gap between the axially adjacent windings of the wire rod 31 of the second sparse pitch portion 83 decreases, and the second sparse pitch portion 83 shrinks in the axial direction. Next, if the shaft portion 11 is released while the proximal end of the deformation portion 81 is held, as illustrated in FIG. 11(C), the second sparse pitch portion 83 stretches or expands in the axial direction due to the self-restorative force. In this manner, the dense pitch portion 82 and the sparse pitch portion 34 of the deformation portion 81 move to the distal side, and the puncture portion 15 fixed to the deformation portion 81 by the second fixing portion 36 moves to distal side. In this manner, the stretching or expanding force of the deformation portion 81 (second sparse pitch portion 83) is used. While the sparse pitch portion 34 is caused to shrink inside the dilator 40, the puncture portion 15 is caused to protrude, thereby enabling the biological tissue to be punctured.

Figure 12A:
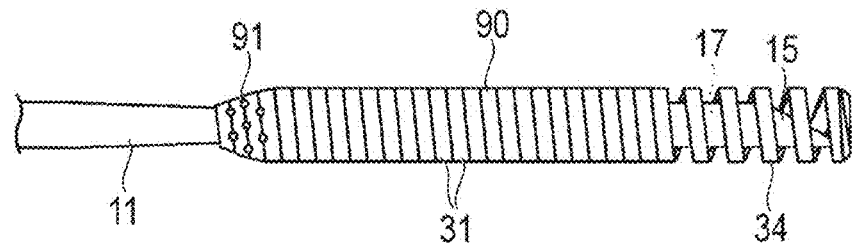
FIGS. 12(A) and 12(B) are plan views illustrating modification examples.

In addition, as in a third modification example illustrated in FIG. 12(A), a plurality of circulation holes 91 may be formed in a proximal portion of a deformation portion 90. For example, the circulation holes 91 are formed in an edge portion of the axial windings of the wire rod 31 aligned with each other in the axial direction, but a form of the holes is not limited. The circulation holes 91 are formed in the proximal portion of the deformation portion 90. Accordingly, even if the spirals windings of the wire rod 31 are dense (even if there is no gap between the windings of the wire rod 31 aligned with each other in the axial direction), the fluid is easily circulated between the inner peripheral surface and the outer peripheral surface of the deformation portion 90. In this manner, the contrast agent or blood can be satisfactorily circulated via the through-hole 17 of the puncture portion 15, the gap between the deformation portion 90 and the shaft portion 11, and the circulation holes 91. Then, the windings of the wire rod 31 of the proximal portion of the deformation portion 90 are densely arranged without any gap. Accordingly, the force can be effectively transmitted in the axial direction inside the dilator 40. A position for forming the circulation holes 91 of the deformation portion 90 is not limited to the proximal portion.

Figure 12B:
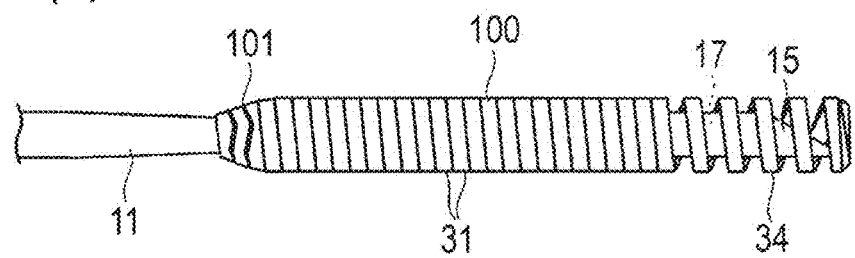

In addition, as in a fourth modification example illustrated in FIG. 12(B), an edge portion of the wire rod 31 in a proximal portion of a deformation portion 100 may have a shape having irregularities 101. In this manner, a gap is likely to be formed in the edge portion of the wire rod 31 in the proximal portion of the deformation portion 100. A shape of the irregularities 101 in the edge portion of the wire rod 31 is not particularly limited. The irregularities 101 are formed in the edge portion of the wire rod 31 of the deformation portion 100. Accordingly, the fluid is easily circulated between the inner peripheral surface and the outer peripheral surface of the deformation portion 100. In this manner, the contrast agent or the blood is satisfactorily circulated via the through-hole 17 of the puncture portion 15, the gap between the deformation portion 100 and the shaft portion 11, and the gaps between the windings of the wire rod 31. A position for forming the irregularities 101 of the deformation portion 100 is not limited to the proximal portion.

Figure 13A:
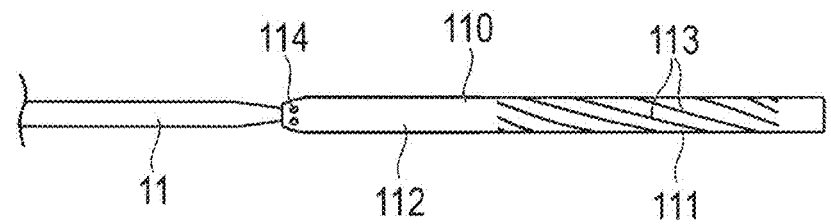
FIGS. 13(A) and 13(B) are plan views illustrating a fifth modification example.
Figure 13B:
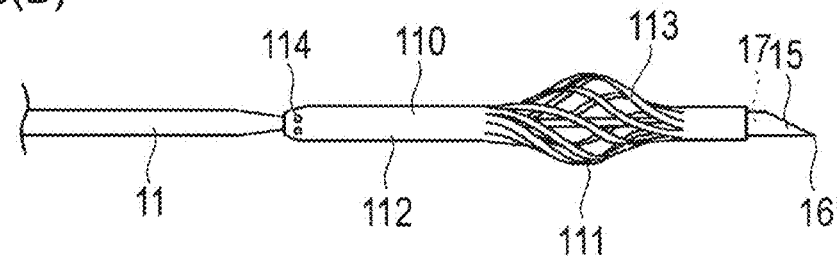

In addition, as in a fifth modification example shown in FIG. 13(A), a deformation portion 110 includes a distal deformation portion 111 expandable in the radial direction in the dilator 40 by a distal end of the deformation portion 110 contacting the fossa ovalis and moving in the axial direction in the dilator 40, and a tubular proximal deformation portion 112. The distal deformation portion 111 has a plurality of spirally wound slits 113. The slits 113 penetrate between the inner peripheral surface and the outer peripheral surface of the distal deformation portion 111. The proximal deformation portion 112 is an elastically deformable tubular member, and a plurality of circulation holes 114 are formed in the proximal portion. The circulation holes 114 are formed in the proximal portion of the deformation portion 110. Accordingly, the fluid is easily circulated between the inside and the outside of the deformation portion 110. In this manner, the contrast agent or blood can be satisfactorily circulated via the through-hole 17 of the puncture portion 15, the gap between the deformation portion 110 and the shaft portion 11, and the circulation holes 114. A position for forming the circulation holes 114 of the deformation portion 110 is not limited to the proximal portion. The deformation portion 110 according to the fifth modification example shrinks in the axial direction inside the dilator 40. In this manner, as illustrated in FIG. 13(B), the slit 113 is widened, and the deformation portion 110 stretches in the radial direction within a range of the lumen of the dilator 40. Therefore, if the distal end of the deformation portion 110 receives the force acting toward the proximal side, the deformation portion 110 stretches outward in the radial direction while shrinking or shortening in the axial direction. Therefore, after the needle portion 16 penetrates the biological tissue, the distal deformation portion 111 stretching in the radial direction passes through the hole of the biological tissue, thereby enabling the hole to be widened.

Figures 14A, 14B:
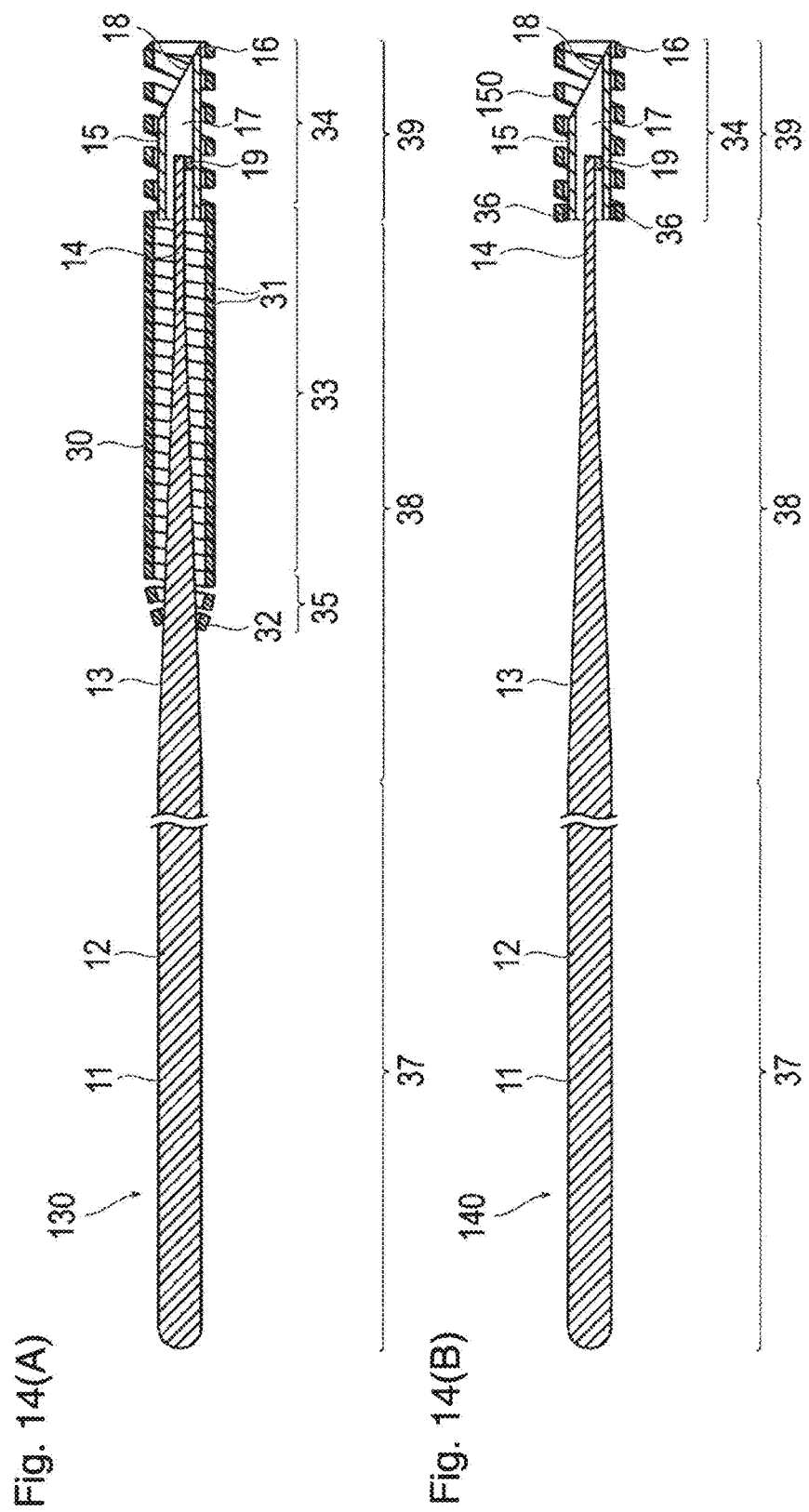
FIGS. 14(A) and 14(B) are sectional views illustrating modification examples.

In addition, as in a sixth modification example illustrated in FIG. 14(A), the guide wire 130 may not have the second fixing portion 36 for fixing the deformation portion 30 and the puncture portion 15 to each other. That is, the deformation portion 30 and the puncture portion 15 may not be fixed to each other. In this manner, the guide wire intermediate portion 38 can be more flexible.

In addition, as in a seventh modification example illustrated in FIG. 14(B), a deformation portion 150 of a guide wire 140 may not have the dense pitch portion 33 and the proximal diameter decreasing portion 35 on the proximal side of the second fixing portion 36 to be fixed to the puncture portion 15. In this manner, the guide wire intermediate portion 38 can be more flexible. The distal portion of the shaft portion 11 is not covered by the deformation portion 30. Accordingly, when the shaft portion 11 is accommodated inside the inserter 60 or the dilator 40, there is a possibility that the shaft portion 11 may be deflected as much as the inner diameter of the inserter 60 or the dilator 40. However, even if the shaft portion 11 is deflected as much as the inner diameter of the inserter 60 or the dilator 40, force transmitting power is weakened. However, while the sparse pitch portion 34 is caused to shrink or shorten in the axial direction, the sparse pitch portion 34 can be pushed into the distal side.

Figure 15A:
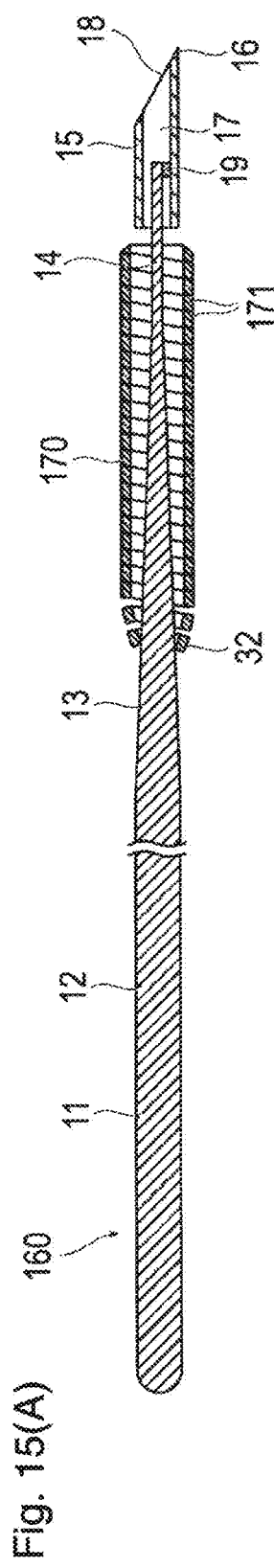
FIGS. 15(A) and 15(B) are sectional views illustrating modification examples.

In addition, as in an eighth modification example illustrated in FIG. 15(A), a deformation portion 170 of a guide wire 160 is not fixed to the puncture portion 15, and may be fixed to the shaft diameter decreasing portion 13 of the shaft portion 11 by the first fixing portion 32. The first fixing portion 32 is located in the proximal portion of the deformation portion 170. The distal end of the deformation portion 170 is located on the proximal side from the puncture portion 15. Therefore, the deformation portion 170 does not accommodate the puncture portion 15. Spiral windings of the wire rod 171 of the deformation portion 170 which are aligned with each other in the axial direction may be in contact with each other, or may not be in contact with each other. If the guide wire 160 is located inside the elongated body such as the dilator 40, the deformation portion 170 does not surround the puncture portion 15. However, the outer diameter decreases toward the distal side, and the deformation portion 170 can surround the shaft portion 11 having low rigidity. Therefore, the deformation portion 170 decreases the gap by compensating for the periphery of the shaft portion 11 which is likely to be deflected due to the lowered rigidity, and prevents the shaft portion 11 from being deflected inside the elongated body such as the dilator 40. Therefore, the deformation portion 170 prevents the movement of the guide wire 180 in the axial direction inside the dilator 40 from being absorbed by the shaft portion 11 which is likely to be deflected. Therefore, the biological tissue can be effectively punctured by the puncture portion 15 fixed to the shaft portion 11. In addition, if the guide wire 160 is located outside the elongated body such as the dilator 40, the deformation portion 170 does not surround the puncture portion 15. However, the deformation portion 170 can be freely deflected together with the shaft portion 11 having the low rigidity. Therefore, if the puncture portion 15 comes into contact with the biological tissue and the distal end of the puncture portion 15 receives the force acting toward the proximal side, the shaft portion 11 and the deformation portion 170 are deflected, and the force escapes to other portions from the puncture portion 15. Therefore, in a state where the guide wire 160 is located outside the elongated body such as the dilator 40, the biological tissue can be prevented from being damaged by the puncture portion 15, and the safety can be improved. Therefore, the guide wire 160 can be used in order to guide the dilator 40, even if the needle portion 16 is exposed without being accommodated in the deformation portion 170.

Figure 15B:
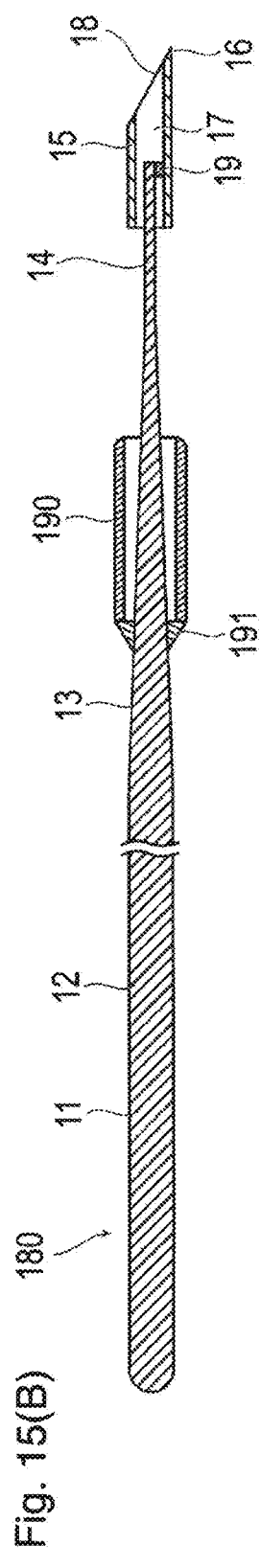

In addition, as in a ninth modification example illustrated in FIG. 15(B), a deformation portion 190 of a guide wire 180 is not a spiral winding but a tubular body. Without being fixed to the puncture portion 15, the deformation portion 190 may be fixed to the shaft diameter decreasing portion 13 of the shaft portion 11 by a first fixing portion 191. The deformation portion 190 is formed of a material which is flexibly deformable in synchronization with the shaft portion 11. For example, the deformation portion 190 may be a flexible resin tube. The first fixing portion 191 is located in the proximal portion of the deformation portion 190. The distal end of the deformation portion 190 is located on the proximal side from the puncture portion 15. Therefore, the deformation portion 190 does not accommodate the puncture portion 15. If the guide wire 180 is located inside the elongated body such as the dilator 40, the deformation portion 190 does not surround the puncture portion 15. However, the outer diameter decreases toward the distal side, and the deformation portion 190 can surround the shaft portion 11 having the low rigidity. Therefore, the deformation portion 190 decreases the gap by compensating for the periphery of the shaft portion 11 which is likely to be deflected due to the lowered rigidity, and prevents the shaft portion 11 from being deflected inside the elongated body such as the dilator 40. Therefore, the deformation portion 190 prevents the movement of the guide wire 180 in the axial direction inside the dilator 40 from being absorbed by the shaft portion 11 which is likely to be deflected. Therefore, the biological tissue can be effectively punctured by the puncture portion 15 fixed to the shaft portion 11. In addition, if the guide wire 180 is located outside the elongated body such as the dilator 40, the deformation portion 190 does not surround the puncture portion 15. However, the deformation portion 190 can be freely deflected together with the shaft portion 11 having the low rigidity. Therefore, if the puncture portion 15 comes into contact with the biological tissue and the distal end of the puncture portion 15 receives the force acting toward the proximal side, the shaft portion 11 and the deformation portion 190 are deflected, and the force escapes to other portions from the puncture portion 15. Therefore, in a state where the guide wire 180 is located outside the elongated body such as the dilator 40, the biological tissue can be prevented from being damaged by the puncture portion 15, and the safety can be improved. Therefore, the guide wire 180 can be used in order to guide the dilator 40, even if the needle portion 16 is exposed without being accommodated in the deformation portion 190.

Also, as in a tenth modification example illustrated in FIG. 16(A), a deformation portion 210 of a guide wire 200 may be accommodated in the puncture portion 15 without accommodating the puncture portion 15. The deformation portion 210 internally has the distal portion of the shaft portion 11. The distal end of the deformation portion 210 is located on the distal side from the puncture portion 15, and the proximal end of the deformation portion 210 is located on the proximal side from the puncture portion 15. The deformation portion 210 is fixed to the shaft diameter decreasing portion 13 by a first fixing portion 211 located in the proximal portion. In addition, the deformation portion 210 is fixed to the puncture portion 15 by a second fixing portion 212 located on the distal side from the first fixing portion 211. Furthermore, the deformation portion 210 is fixed to the distal end of the shaft portion 11 by a third fixing portion 213 located on the distal side from the second fixing portion 212. Therefore, the shaft portion 11 is indirectly fixed to the puncture portion 15 via the deformation portion 210. The deformation portion 210 has a sparse pitch portion 215 having a gap between the wire rods 214 aligned with each other in the axial direction, on the distal side from the third fixing portion 213. In addition, the deformation portion 210 has a dense pitch portion 216 whose inter-pitch distance is shorter than the sparse pitch portion 215, on the proximal side from the third fixing portion 213. The inter-pitch distance of the dense pitch portion 216 is not particularly limited, and may be equal to or longer than the inter-pitch distance of the sparse pitch portion 215. A portion protruding to the distal side from the puncture portion 15 of the deformation portion 210 is the sparse pitch portion 215. If the guide wire 160 is located inside the elongated body such as the dilator 40, the proximal portion of the deformation portion 210 can surround the shaft portion 11 having the low rigidity. Therefore, the deformation portion 210 decreases the gap by compensating for the periphery of the shaft portion 11 which has the low rigidity and which is likely to be deflected, and prevents the shaft portion 11 from being deflected inside the elongated body such as the dilator 40. In addition, a portion accommodated in the puncture portion 15 of the deformation portion 210, or a portion located on the distal side from the puncture portion 15 of the deformation portion 210 decreases the gap by compensating the internal space of the elongated body such as the dilator 40. Accordingly, the shaft portion 11 is prevented from being deflected inside the elongated body such as the dilator 40. Therefore, the deformation portion 210 prevents the movement of the guide wire 200 in the axial direction inside the dilator 40 from being absorbed by the shaft portion 11 which is likely to be deflected. Therefore, if the guide wire 200 is caused to protrude from the dilator 40, as illustrated in FIG. 16(B), the distal end of the sparse pitch portion 215 located on the distal side from the puncture portion 15 moves to the proximal side. In this manner, the biological tissue can be effectively punctured by the puncture portion 15 indirectly fixed to the shaft portion via the deformation portion 210. In addition, if the guide wire 160 is located outside the elongated body such as the dilator 40, as illustrated in FIG. 16(A), the sparse pitch portion 215 is located on the distal side from the puncture portion 15, thereby preventing the biological tissue from being damaged by the puncture portion 15. Furthermore, a portion covering the shaft portion 11 of the deformation portion 210 can be freely deflected together with the shaft portion 11 having the low rigidity. Therefore, if the distal end of the sparse pitch portion 215 or the puncture portion 15 comes into contact with the biological tissue and the distal end of the sparse pitch portion 215 or the puncture portion 15 receives the force acting toward the proximal side, the shaft portion 11 and the deformation portion 210 are deflected, and the force escapes to a portion different from the puncture portion 15. Therefore, in a state where the guide wire 200 is located outside the elongated body such as the dilator 40, the biological tissue can be prevented from being damaged by the puncture portion 15, and the safety can be improved. Therefore, the guide wire 200 can be used in order to guide the dilator 40. The first fixing portion 211 of the deformation portion 210 may be located inside the puncture portion 15 without being located on the distal side of the puncture portion 15. Therefore, the first fixing portion 211 may be fixed to the shaft distal portion 14.

Figure 17:
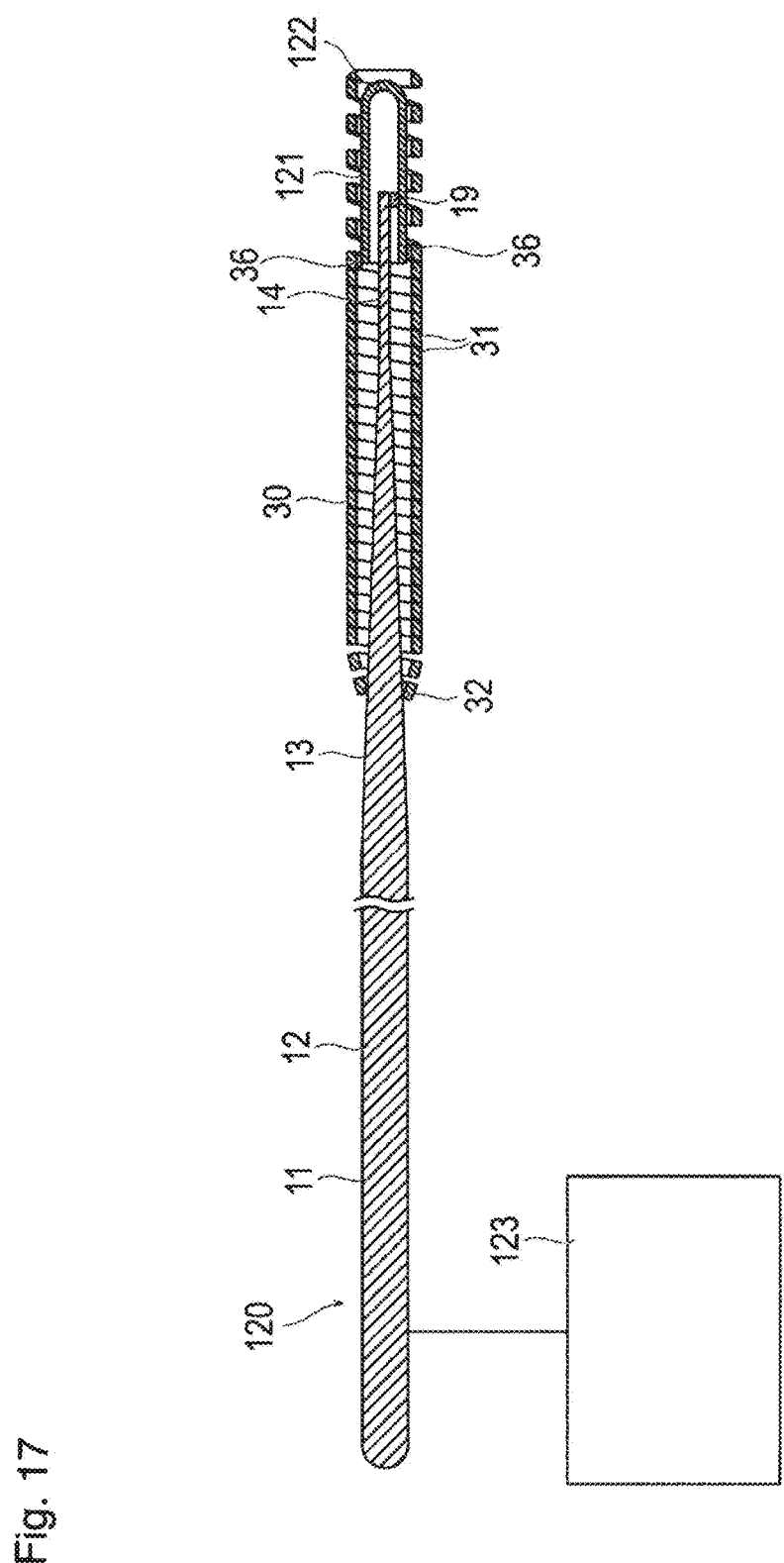
FIG. 17 is a sectional view illustrating an eleventh modification example.

In addition, as in an eleventh modification example illustrated in FIG. 17, a puncture portion 121 of a guide wire 120 may have a needle portion 122 which is a radio frequency needle (RF Needle) for supplying radio frequency energy. The puncture portion 121, the shaft portion 11, and the needle fixing portion 19 are formed of a conductive member. The deformation portion 30 is formed of an insulator. Alternatively, the deformation portion 30 may be formed by coating the conductive member with an insulating resin. For example, a shape of the end surface on the distal side of the needle portion 122 is a hemispherical shape, but is not particularly limited. The proximal portion of the shaft portion 11 can be electrically connected to an I/O (input/output) device 123 (for example, a console) that supplies the radio frequency energy. Therefore, the radio frequency energy is supplied to the needle portion 122 from the I/O device 123 via the shaft portion 11 and the needle fixing portion 19.

In a case of using the guide wire 120 according to the eleventh modification example, the needle portion 122 of the guide wire 120 is accommodated in the dilator 40. In a state where the dilator 40 is pressed against the fossa ovalis O, the radio frequency energy is supplied to the puncture portion 121 from the I/O device 123. Thereafter, if the guide wire 120 is pushed into the distal side, as illustrated in FIG. 18(A), the deformation portion 30 shrinks or shortens in the axial direction, and the needle portion 122 comes into contact with the fossa ovalis O. In this manner, the fossa ovalis O is ablated by the needle portion 122, thereby forming the hole. If the needle portion 122 penetrates the fossa ovalis O, as illustrated in FIG. 18(B), the deformation portion 30 stretches to the distal side, and the needle portion 122 is accommodated in the deformation portion 30. In this manner, the puncture portion 121 can be prevented from erroneously puncturing an unintended position. In addition, in the case of using the guide wire 120 according to the eleventh modification example, the safety is ensured by the deformation portion 30 accommodating the puncture portion 121. Accordingly, the I/O device 123 does not need a safety mechanism that controls the supply of the radio frequency energy by being incorporated in the console of the RF needle in the related art. Therefore, a more versatile console such as a console for an electric scalpel can be used for the I/O device 123.

In addition, as in a twelfth modification example illustrated in FIG. 19, a deformation portion 230 of a guide wire 220 may include a sparse pitch portion 231 and a dense pitch portion 232 located on the distal side from the sparse pitch portion 231. In the description below, features that are the same or similar to those described above are identified by the same reference numerals and a detailed description of such features is not repeated.

The sparse pitch portion 231 has a longer spiral inter-pitch distance than the dense pitch portion 232. The proximal side of the deformation portion 230, that is, the first fixing portion 32 located on the proximal side of the sparse pitch portion 231 is fixed to the shaft portion 11. The deformation portion 230 is not fixed to the puncture portion 15. The sparse pitch portion 231 can shrink or shorten in the axial direction so as to decrease the gap between the windings of the wire rod 31 aligned with each other in the axial direction. The sparse pitch portion 231 surrounds a portion of the shaft portion 11. The dense pitch portion 232 surrounds the puncture portion 15 and a portion of the shaft portion 11.

Figure 20A:
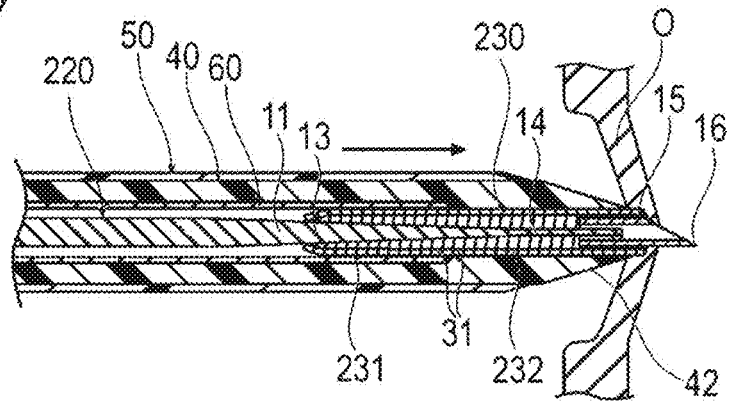
FIGS. 20(A) and 20(B) are sectional views illustrating a state when puncture is performed according to the twelfth modification example.

In a case of using the guide wire 220 according to the twelfth modification example, the guide wire 220 is accommodated in the inserter 60, the dilator 40, and the outer sheath 50. In a state where the dilator 40 is pressed against the fossa ovalis O, the guide wire 220 is pushed into the distal side or in the distal direction. If the distal end of the guide wire 220 comes into contact with the fossa ovalis O, the force acting toward the proximal side is applied to the distal end of the deformation portion 230 located in the most distal portion of the guide wire 220. The deformation portion 230 is accommodated inside the inserter 60 and the dilator 40 so that the deflection is restricted. The deformation portion 230 decreases the gap by compensating for the periphery of the shaft portion 11 which is likely to be deflected due to the lowered rigidity, and prevents the shaft portion 11 from being deflected inside the dilator 40 or the inserter 60. Therefore, as illustrated in FIG. 20(A), the distal end of the sparse pitch portion 231 of the deformation portion 230 receives the force acting toward the proximal side. In this manner, the sparse pitch portion 231 of the deformation portion 230 elastically shrinks or shortens in the axial direction so as to decrease the gap between the wire rods 31. If the deformation portion 230 shrinks or shortens in the axial direction by coming into contact with the fossa ovalis O, the needle portion 16 of the puncture portion 15 accommodated in the deformation portion 230 is exposed. The puncture portion 15 exposed from the deformation portion 230 forms the hole in the fossa ovalis O.

Figure 20B:
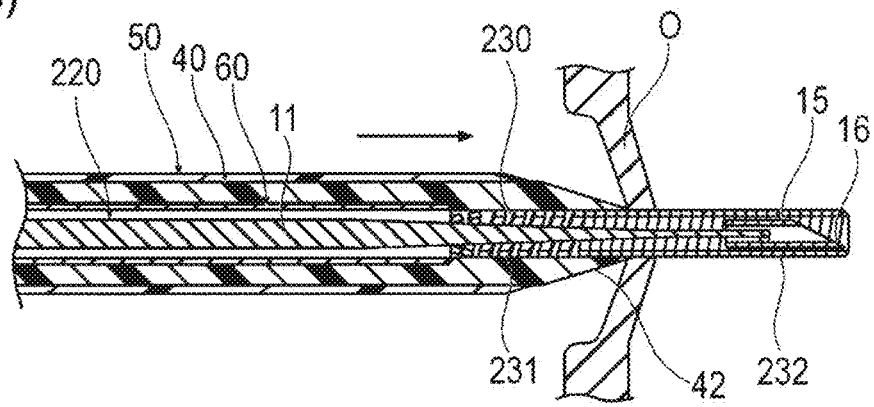

If the distal end of the deformation portion 230 penetrates the hole, as illustrated in FIG. 20(B), the elastically shrunk or shortened deformation portion 230 stretches in the axial direction due to the self-restorative force. In this manner, the puncture portion 15 is accommodated in the deformation portion 230. The deformation portion 230 accommodating the puncture portion 15 protrudes from the dilator 40. Accordingly, the deflection is not restricted, and the deformation portion 230 can be freely deflected. Therefore, the puncture portion 15 inside the left atrium L maintains a state of being accommodated in the deformation portion 230. Therefore, the puncture portion 15 can be prevented from erroneously puncturing an unintended position. Thereafter, the dilator 40 and the outer sheath 50 can be pushed into the hole of the fossa ovalis O along the guide wire 220. In this manner, the hole of the fossa ovalis O is widened.

Figure 21:
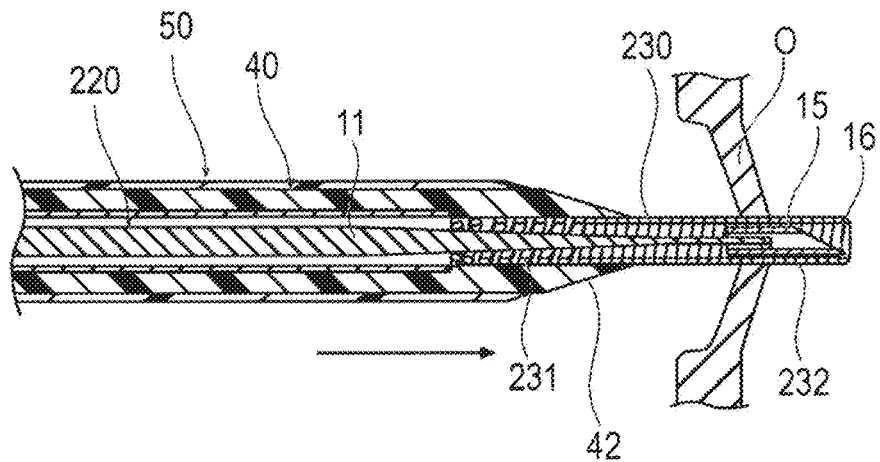
FIG. 21 is a sectional view illustrating a state where the dilator is separated from the fossa ovalis after the guide wire is inserted into the hole of the fossa ovalis.

Before the dilator 40 and the outer sheath 50 are pushed into the hole of the fossa ovalis O, due to the reaction generated when the guide wire 220 is pushed into the hole, there is a possibility that the dilator 40 may be separated from the fossa ovalis O as illustrated in FIG. 21. Heart beats or the force received by the dilator 40 from the blood flow inside the heart may also cause the dilator 40 to be separated from the fossa ovalis O. In this case, the sparse pitch portion 231 of the deformation portion 230 is located on the proximal side from the dense pitch portion 232. Accordingly, the deformation portion 230 is less likely to be exposed on the distal side from the dilator 40. That is, there is a high possibility that a portion of the deformation portion which is exposed to the distal side from the dilator 40 may be the dense pitch portion 232. The dense pitch portion 232 is less likely to be bent than the sparse pitch portion 231. Accordingly, the guide wire 220 can be prevented from being bent between the dilator 40 and the fossa ovalis O. Therefore, even if the dilator 40 is separated from the fossa ovalis O, the dilator 40 and the outer sheath 50 are easily pushed into the hole of the fossa ovalis O along the guide wire 220. In addition, the dense pitch portion 232 having a smaller gap between the axially adjacent windings of the wire rod 31 than the sparse pitch portion 231 covers the puncture portion 15. Accordingly, the puncture portion 15 can be prevented from protruding from the gap between the windings of the wire rod 31, thereby improving the safety.

Figure 22A:
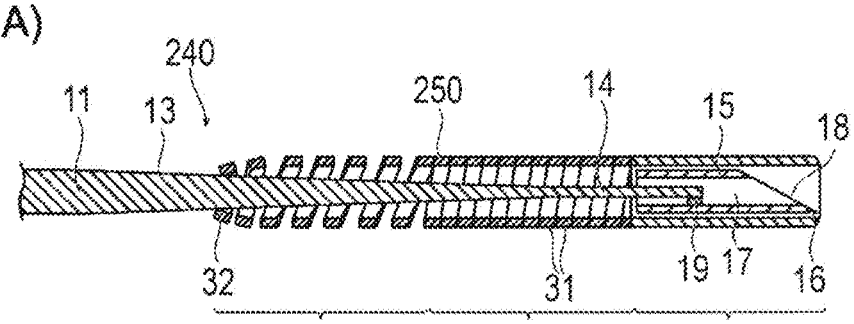
FIGS. 22(A) and 22(B) are sectional views illustrating a thirteenth modification example.

In addition, as in a thirteenth modification example illustrated in FIG. 22(A), a deformation portion 250 of a guide wire 240 may include a sparse pitch portion 251, a dense pitch portion 252 on the distal side from the sparse pitch portion 251, and a distal tube 253 on the distal side from the dense pitch portion 252. In the description below, features that are the same or similar to those described above are identified by the same reference numerals and a detailed description of such features is not repeated.

The sparse pitch portion 251 has a longer spiral inter-pitch distance than the dense pitch portion 252. The proximal side of the deformation portion 250, that is, the first fixing portion 32 located on the proximal side of the sparse pitch portion 251 is fixed to the shaft portion 11. The deformation portion 250 is not fixed to the puncture portion 15. The sparse pitch portion 251 can shrink or shorten in the axial direction so as to decrease the gap between the axially adjacent windings of the wire rod 31 aligned with each other in the axial direction. The sparse pitch portion 251 and the dense pitch portion 252 surround a portion of the shaft portion 11. The dense pitch portion 252 surrounds the puncture portion 15 and a portion of the shaft portion 11. The distal tube 253 is a circular or cylindrical tube fixed to the distal portion of the dense pitch portion 252. The distal tube 253 surrounds the puncture portion 15 and a portion of the shaft distal portion 14 located inside the puncture portion 15. The dense pitch portion 252 may surround the puncture portion 15, and the distal tube 253 may be located on the distal side from the puncture portion 15. The distal tube 253 has higher flexural rigidity than the sparse pitch portion 251 and the dense pitch portion 252 which have the spiral shape.

A material for fabricating the distal tube 253 is preferably provided with rigidity to some extent. For example, it is possible to preferably use a shape memory alloy that exhibits a shape memory effect or super-elasticity when heated, metal such as stainless steel, tantalum, titanium, platinum, gold, and tungsten, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide.

Figure 22B:
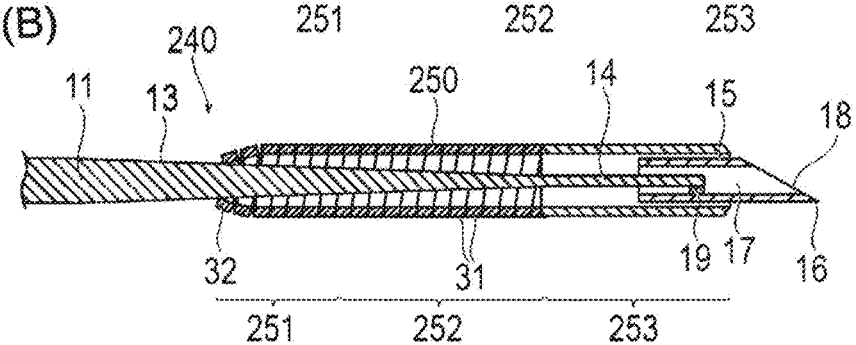

If the guide wire 240 is caused to protrude from the dilator 40 and the distal end of the guide wire 240 comes into contact with the biological tissue, the force acting toward the proximal side is applied to the distal end of the deformation portion 250 located in the most distal portion of the guide wire 240. In this manner, as illustrated in FIG. 22(B), the gap between the axially adjacent windings of the wire rod 31 of the sparse pitch portion 251 decreases, and the sparse pitch portion 251 shrinks or shortens in the axial direction. In this manner, the dense pitch portion 252 and the distal tube 253 of the deformation portion 250 move to the proximal side, thereby exposing the needle portion 16 of the puncture portion 15 accommodated in the deformation portion 250. In this case, the proximal portion of the puncture portion 15 is surrounded by the distal tube 253 having high rigidity. Therefore, the puncture portion 15 is supported by the distal tube 253 of the deformation portion 250, and thus, a posture thereof is stabilized. Therefore, in the guide wire 240, the hole can be smoothly formed in the biological tissue by the puncture portion 15.

Figure 23A:
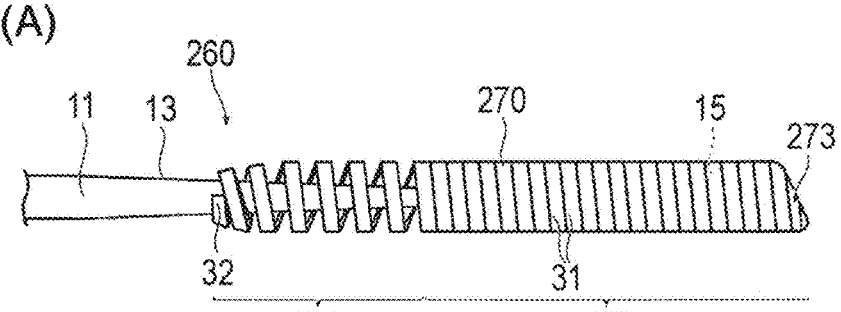
FIGS. 23(A) and 23(B) are views illustrating a guide wire according to a fourteenth modification example.
Figure 23B:
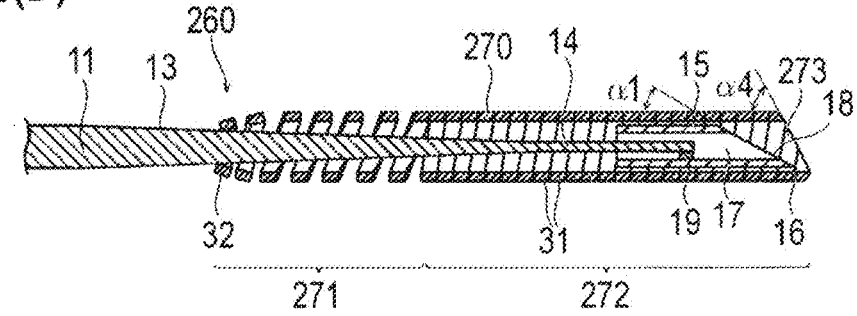

In addition, as in a fourteenth modification example illustrated in FIG. 23(A), a deformation portion 270 of a guide wire 260 may include a sparse pitch portion 271 and a dense pitch portion 272 on the distal side from the sparse pitch portion 271. In the description below, features that are the same or similar to those described above are identified by the same reference numerals and a detailed description of such features is not repeated.

The sparse pitch portion 271 has a longer spiral inter-pitch distance than the dense pitch portion 272. The proximal side of the deformation portion 270, that is, the first fixing portion 32 located on the proximal side of the sparse pitch portion 271 is fixed to the shaft portion 11. The deformation portion 270 is not fixed to the puncture portion 15. The sparse pitch portion 271 can stretch or lengthen in the axial direction so as to decrease the gap between the axially adjacent windings of the wire rod 31 aligned with each other in the axial direction. The sparse pitch portion 271 surrounds a portion of the shaft portion 11. The dense pitch portion 272 surrounds the puncture portion 15 and a portion of the shaft portion 11. The distal end of the dense pitch portion 272 includes an inclined portion 273 inclined to the central axis of the deformation portion 270. An inclined direction of the inclined portion 273 with respect to the central axis of the deformation portion 270 preferably coincides with an inclined direction of the inclined surface 18 with respect to the central axis of the puncture portion 15. However, the inclination angles of the inclined portion 273 and the inclined surface 18 may not be coincident with each other. An inclusion angle α4 of the inclined portion 273 with respect to the central axis of the deformation portion 270 is larger than the inclination angle α1 of the inclined surface 18 with respect to the central axis of the puncture portion 15. Therefore, the end portion of the inclined portion 273 is not sharper than the needle portion 16. The inclined portion 273 is brazed so as to fill the gap between the axially adjacent windings of the wire rod 31 and thus connect the axially adjacent windings of the wire rod 31. Alternatively, the windings of the wire rod 31 may be welded by bringing the axially adjacent windings of the wire rod 31 into contact with each other. Thereafter, the welded wire rod 31 are cut so as to be inclined. The outer edge portion is subjected to curved surface processing, and is smoothly formed.

Figure 24A:
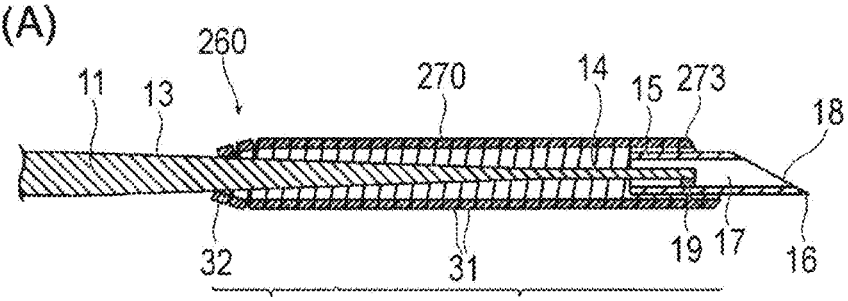
FIGS. 24(A) and 24(B) are sectional views illustrating modification examples.

If the guide wire 260 is caused to protrude from the dilator 40 and the distal end of the guide wire 260 comes into contact with the biological tissue, the force acting toward the proximal side is applied to the distal end of the deformation portion 270 located in the most distal portion of the guide wire 260. In this manner, as illustrated in FIG. 24(A), the gap between the axially adjacent windings of the wire rod 31 of the sparse pitch portion 271 decreases, and the sparse pitch portion 271 shrinks or shortens in the axial direction. In this manner, the dense pitch portion 272 of the deformation portion 270 moves to the proximal side, thereby exposing the needle portion 16 of the puncture portion 15 accommodated in the deformation portion 270. In this case, the proximal portion of the puncture portion 15 is surrounded by the inclined portion 273 of the deformation portion 270 to which the axially adjacent windings of the wire rod 31 are fixed. Therefore, the puncture portion 15 is supported by the inclined portion 273 having relatively high rigidity, and thus, a posture of the puncture portion 15 is stabilized. Therefore, in the guide wire 260, the hole can be smoothly formed in the biological tissue by the puncture portion 15.

Figure 24B:
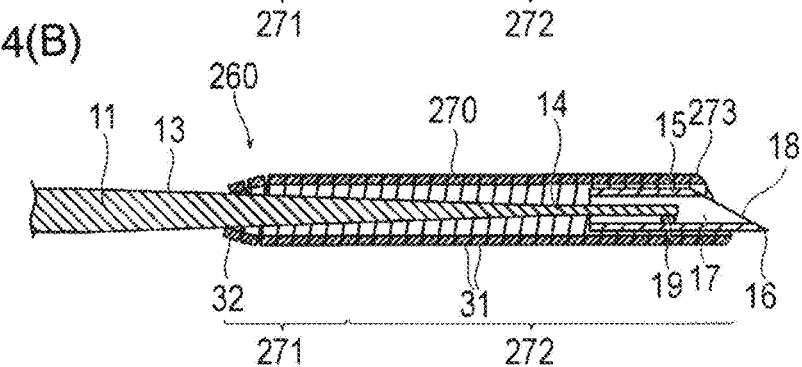

Subsequently to the puncture portion 15, the shrunk deformation portion 270 is pushed into the hole formed by the puncture portion 15. The inclined portion 273 is disposed in the distal end of the deformation portion 270. Accordingly, a weak force enables the deformation portion 270 to smoothly pass through the hole of the biological tissue with a small force. In this case, the distal end of the deformation portion 270 in a shrunk or shortened state coincides with the proximal end of the inclined surface 18 of the puncture portion 15, or is located on the proximal side from the proximal end. In this manner, the inclined portion 273 reaches the biological tissue after the inclined surface 18 of the puncture portion 15 passes through the biological tissue. Therefore, the weak force enables the deformation portion 270 to smoothly widen the hole of the biological tissue. In addition, the inclined direction of the inclined portion 273 coincides with the inclined direction of the inclined surface 18. Accordingly, the deformation portion 270 can smoothly and largely widen the hole of the biological tissue formed by the puncture portion 15. As in a fifteenth modification example illustrated in FIG. 24(B), the distal end of the inclined portion 273 of the deformation portion 270 in a shrunk state may be located on the distal side from the proximal end, which is the proximal side from the distal end of the inclined surface 18 of the puncture portion 15. In this case, the amount of the sharp needle portion 16 exposed from the deformation portion 270 can be minimized, and the movement distance until the shrunk deformation portion 270 completely covers the needle portion 16 again can be shortened, thereby improving the safety. The inclined portion 273 of the deformation portion 270 is formed using the wire rod 31. However, for example, the inclined portion may be formed by fixing other members to the wire rod 31.

Figure 25A:
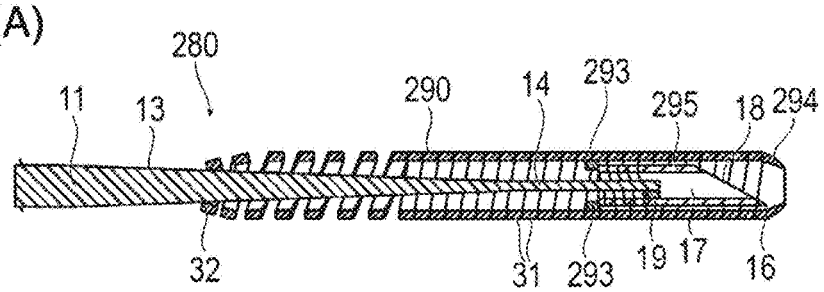
FIGS. 25(A) and 25(B) are sectional views illustrating a sixteenth modification example.

In addition, as in a sixteenth modification example illustrated in FIG. 25(A), a deformation portion 290 of a guide wire 280 may include a sparse pitch portion 291, a dense pitch portion 292 on the distal side from the sparse pitch portion 251, a first stopper 293, and a second stopper 294. In the description below, features that are the same or similar to those described above are identified by the same reference numerals and a detailed description of such features is not repeated.

The sparse pitch portion 291 has a longer spiral inter-pitch distance than the dense pitch portion 292. The proximal side of the deformation portion 290, that is, the first fixing portion 32 located on the proximal side of the sparse pitch portion 291 is fixed to the shaft portion 11. The deformation portion 290 has at least one first stopper 293 which comes into contact with the proximal end of the puncture portion 295, on the inner peripheral surface of the sparse pitch portion 291. The first stopper 293 restricts the movement of the puncture portion 295 to the proximal side from the first stopper 293. Therefore, for example, when the guide wire 280 is removed from the body, if the deformation portion 290 is pulled to the distal side, the first stopper 293 comes into contact with the proximal end of the puncture portion 295. Therefore, the inter-pitch distance of the wire rod 31 of the deformation portion 290 can be prevented from being excessively widened. Therefore, the needle portion 16 can be prevented from protruding from the gaps between the axially adjacent windings of the wire rod 31, and the deformation portion 290 can be prevented from being detached from the guide wire 280. Accordingly, the safety can be improved.

Figure 25B:
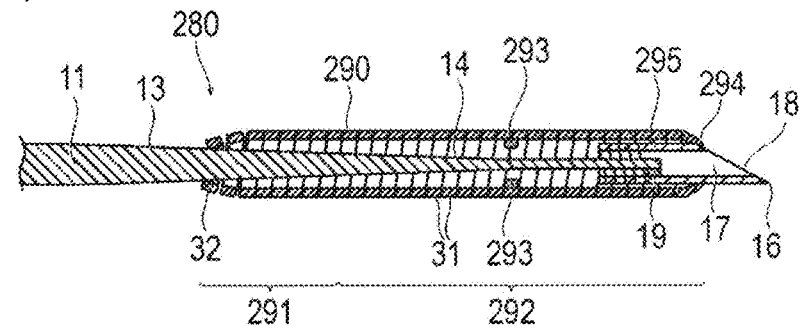

The distal end of the deformation portion 290 has the second stopper 294 whose inner diameter decreases. As illustrated in FIG. 25(B), when the deformation portion 290 shrinks, the second stopper 294 restricts the movement of the whole puncture portion 295 to the distal side from the second stopper 294. Therefore, even in a case where the puncture portion 295 and the shaft portion 11 are unfixed by the needle fixing portion 19, the puncture portion 295 can be prevented from remaining inside the body after being held inside the deformation portion 290.

The proximal portion of the puncture portion 295 is subjected to spiral cutting, and is spirally wound. In this manner, the proximal portion of the puncture portion 295 becomes flexible, and is easily bent. Therefore, the flexural rigidity is smoothly changed between the puncture portion 295 and the shaft portion 11 in the axial direction, and kinks are less likely to occur. In order to have a flexible proximal portion of the puncture portion, a flexible tube may be connected thereto without performing spiral cutting.

Figure 26A:
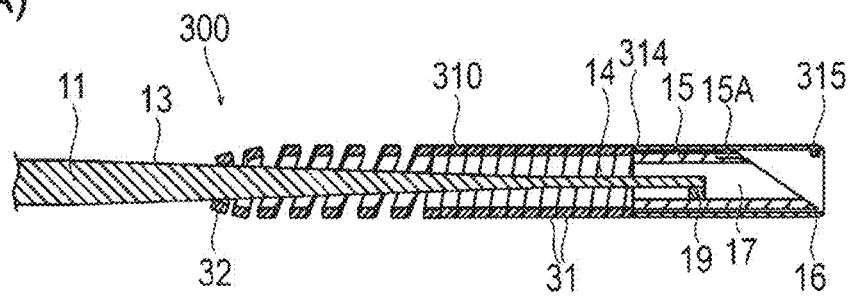
FIGS. 26(A) and 26(B) are sectional views illustrating a seventeenth modification example.

In addition, as in a seventeenth modification example illustrated in FIG. 26(A), a deformation portion 310 of a guide wire 300 may include a sparse pitch portion 311, a dense pitch portion 312 on the distal side from the sparse pitch portion 311, and a distal tube 313 on the distal side from the dense pitch portion 312. In the description below, features that are the same or similar to those described above are identified by the same reference numerals and a detailed description of such features is not repeated.

The sparse pitch portion 311 has a longer spiral inter-pitch distance than the dense pitch portion 312. The proximal side of the deformation portion 310, that is, the first fixing portion 32 located on the proximal side of the sparse pitch portion 311 is fixed to the shaft portion 11. The deformation portion 310 is not fixed to the puncture portion 15. The sparse pitch portion 311 can stretch or lengthen in the axial direction so as to decrease the gaps between the axially adjacent windings of the wire rod 31 aligned with each other in the axial direction. The sparse pitch portion 311 and the dense pitch portion 312 surround a portion of the shaft portion 11. The inner diameter of the dense pitch portion 312 is smaller than the outer diameter of the puncture portion 15. The distal end of the dense pitch portion 312 has a step on the inner peripheral surface, and the step is a first stopper 314 which comes into contact with the proximal end of the puncture portion 15. The first stopper 314 restricts the movement of the puncture portion 15 to the proximal side from the first stopper 314. The distal tube 313 is a circular or cylindrical tube fixed to the distal portion of the dense pitch portion 312. The distal tube 313 has higher flexural rigidity than the sparse pitch portion 311 and the dense pitch portion 312. The distal tube 313 surrounds the puncture portion 15 and a portion of the shaft portion 11. The outer diameter of the distal tube 313 is substantially the same as the outer diameter of the dense pitch portion 312. The inner diameter of the distal tube 313 is larger than the inner diameter of the dense pitch portion 312, and is larger than the outer diameter of the puncture portion 15. Therefore, the distal tube 313 is thinner than the dense pitch portion 312. The distal tube 313 has a second stopper 315 protruding inward in the radial direction, on the inner peripheral surface of the distal portion. In the circumferential direction, the second stopper 315 is located on a side opposite to the position having the needle portion 16 of the puncture portion 15. The puncture portion 15 has a groove portion 15A extending in the proximal direction from the distal end, on the inner peripheral surface of the distal portion. The groove portion 15A is located on the proximal side of the second stopper 315. The second stopper 315 can enter the groove portion 15A from the distal side.

Figure 26B:
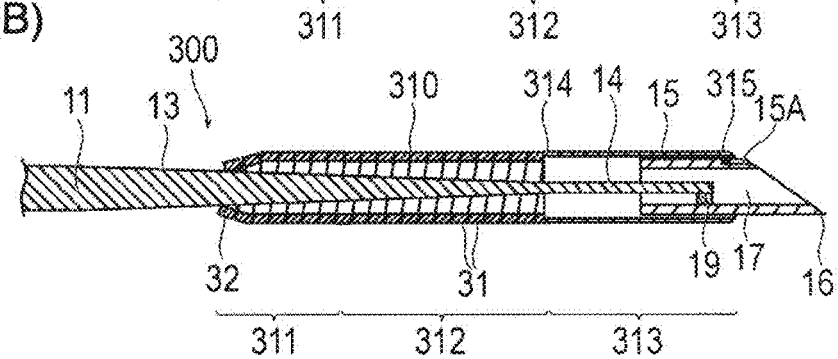

When the guide wire 300 is removed from the body, if the deformation portion 310 is pulled to the distal side, as illustrated in FIG. 26(A), the first stopper 314 comes into contact with the proximal end of the puncture portion 15. Therefore, the inter-pitch distance of the wire rod 31 of the deformation portion 310 can be prevented from being excessively widened. Therefore, the needle portion 16 can be prevented from protruding from the gap between the wire rods 31, and the deformation portion 310 can be prevented from being detached from the guide wire 300. Accordingly, the safety can be improved. In addition, the distal tube 313 is thin. Accordingly, the outer diameter of the puncture portion 15 can be increased so that the puncture portion 15 can largely form the hole in the biological tissue. In addition, the distal tube 313 is thin. Accordingly, after the biological tissue is punctured by the puncture portion 15, the distal tube 313 can be smoothly inserted into the hole of the biological tissue with less resistance. If the deformation portion 310 shrinks and the needle portion 16 of the puncture portion 15 protrudes from the distal tube 313, as illustrated in FIG. 26(B), the second stopper 315 enters the groove portion 15A. If the second stopper 315 reaches the most proximal side of the groove portion 15A, the second stopper 315 comes into contact with the end surface of the groove portion 15A. In this manner, the deformation portion 310 can be prevented from excessively moving rearward from the puncture portion 15, and a proper positional relationship between the deformation portion 310 and the puncture portion 15 can be maintained. Therefore, the biological tissue can be punctured while the deformation portion 310 maintains a desired position for the puncture portion 15.

Figure 27:
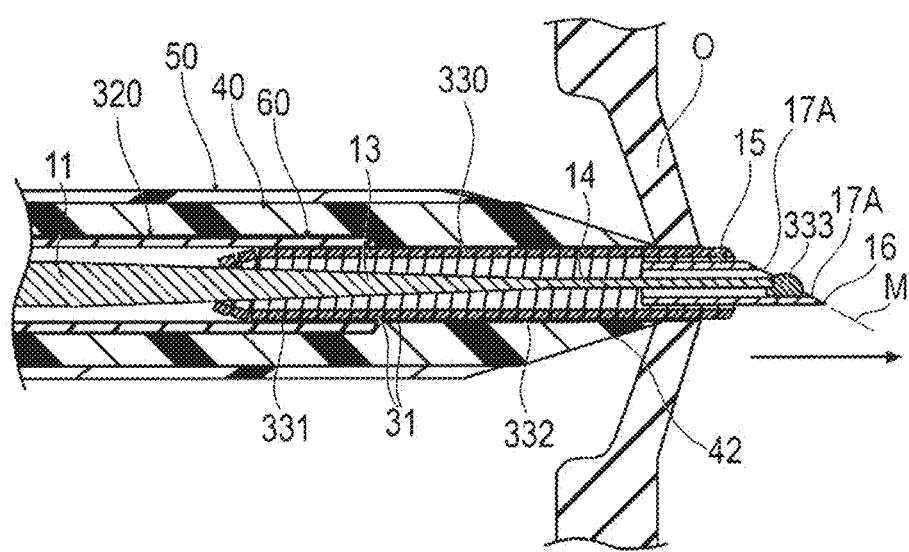
FIG. 27 is a sectional view illustrating a state when puncture is performed according to an eighteenth modification example.

In addition, as in an eighteenth modification example illustrated in FIG. 27, a deformation portion 330 of a guide wire 320 may include a sparse pitch portion 331 and a dense pitch portion 332 on the distal side from the sparse pitch portion 331. In the description below, features that are the same or similar to those described above are identified by the same reference numerals and a detailed description of such features is not repeated.

The sparse pitch portion 331 has a longer spiral inter-pitch distance than the dense pitch portion 332. The proximal side of the deformation portion 330, that is, the first fixing portion 32 located on the proximal side of the sparse pitch portion 331 is fixed to the shaft portion 11. The deformation portion 330 is not fixed to the puncture portion 15. The sparse pitch portion 331 can stretch in the axial direction so as to decrease the gap between the wire rods 31 aligned with each other in the axial direction. The sparse pitch portion 331 surrounds a portion of the shaft portion 11. The dense pitch portion 332 surrounds the puncture portion 15 and a portion of the shaft portion 11. The shaft end of the shaft distal portion 14 is fixed to the inner peripheral surface of the puncture portion 15 through welding or bonding by a needle fixing portion 333. The needle fixing portion 333 protrudes outward of a surface where the inclined surface 18 of the puncture portion 15 is located. That is, the needle fixing portion 333 protrudes outward of a surface M where a ring-shaped inner edge portion 17A of an opening portion is located on the inclined surface 18 of the through-hole 17. The needle fixing portion 333 is located on the proximal side from the distal end of the needle portion 16. A surface shape of a protruding portion 334 protruding from the inclined surface 18 of the needle fixing portion 333 is not particularly limited. However, the surface is preferably smooth without any corner. The needle fixing portion 333 including the protruding portion 334 is disposed so as not to close the through-hole 17 of the puncture portion 15.

Figure 28:
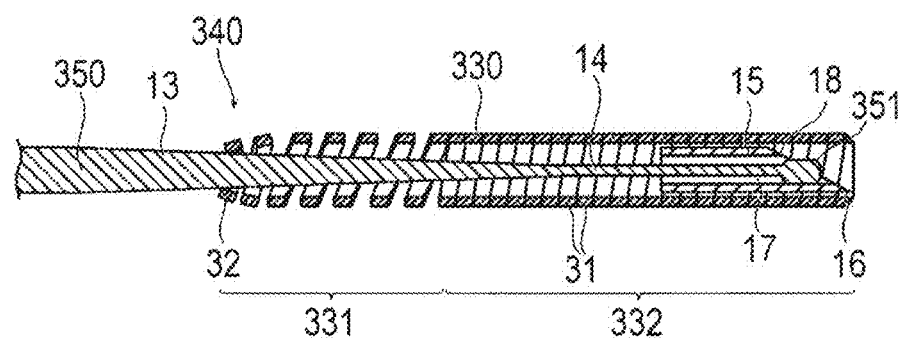
FIG. 28 is a sectional view illustrating a guide wire according to a nineteenth modification example.

If the guide wire 320 is caused to protrude from the dilator 40 and the distal end of the guide wire 320 comes into contact with the biological tissue, the force acting toward the proximal side is applied to the distal end of the deformation portion 330 located in the most distal portion of the guide wire 320. In this manner, the gap between the axially adjacent windings of the wire rod 31 of the sparse pitch portion 331 decreases, and the sparse pitch portion 331 shrinks or shortens in the axial direction. In this manner, the dense pitch portion 332 of the deformation portion 330 moves to the proximal side, and the needle portion 16 is exposed from the deformation portion 330. The needle portion 16 exposed from the deformation portion 330 forms the hole in the biological tissue. In this case, the protruding portion 334 of the needle fixing portion 333 protrudes outward from the surface where the inclined surface 18 of the puncture portion 15 is located. Therefore, when the puncture portion 15 passes through the hole of the biological tissue, the protruding portion 334 largely widens the hole formed by the needle portion 16. Therefore, the resistance decreases when the puncture portion 15 and then the distal end of the deformation portion 330 pass through the biological tissue hole while widening the hole. Therefore, the distal end of the deformation portion 330 can largely widen and smoothly pass through the hole of the biological tissue with less resistance. If the surface of the protruding portion 334 protruding from the inclined surface 18 of the needle fixing portion 333 is smooth without any corner, the protruding portion 334 can more smoothly widen the hole formed by the needle portion 16. Therefore, the distal end of the deformation portion 330 can more smoothly pass through the hole of the biological tissue. As in a nineteenth modification example illustrated in FIG. 28, the protruding portion 351 may be a portion of the distal portion of the shaft portion 350 of the guide wire 340. The protruding portion 351 is fixed to the inner peripheral surface of the puncture portion 15 through welding or bonding. The protruding portion 351 protrudes outward from the surface where the inclined surface 18 of the puncture portion 15 is located. The protruding portion protruding outward from the inclined surface 18 may not be disposed in a portion where the shaft portion 11 and the puncture portion 15 are interlocked with each other. For example, the protruding portion may be a portion of the puncture portion 15.

Figure 29:
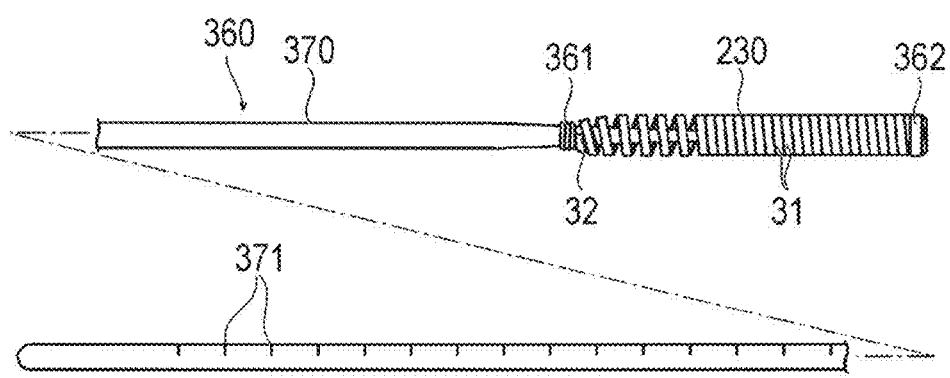
FIG. 29 is a plan view illustrating a guide wire according to a twentieth modification example.

In addition, as in a twentieth modification example illustrated in FIG. 29, a guide wire 360 may include first markers 361 and 362, and a second marker 371. The same reference numerals will be given to elements having the same function as that of the above-described embodiment, and description thereof will be omitted.

The first markers 361 and 362 are used in order to visibly recognize a position of the deformation portion 230 inserted into the living body by using X-rays. The first marker 361 is a wire rod including an X-ray contrast material wound around a position to which the proximal end of the deformation portion 30 of the shaft portion 370 is fixed. The first marker 362 is a ring-shaped member of the X-ray contrast material fixed to the distal end of the deformation portion 230. For example, the X-ray contrast material is preferably formed of at least one metal or two or more alloys in a group including gold, platinum, iridium, tungsten, or an alloy thereof, and a silver-palladium alloy. Since the first marker 361 is provided, under radioscopy, an operator can easily recognize the position of the deformation portion 230 inside the living body. The position where the first marker 361 is provided is not limited to the proximal end of the deformation portion 30. In addition, the first marker 362 is disposed in the distal side from the sparse pitch portion 231 of the deformation portion 230. In this manner, under the radioscopy, the operator can easily recognize the position of the deformation portion 230 which moves relative to the needle portion 16. Therefore, the operator can easily recognize whether or not the deformation portion 230 covers the needle portion 16, and can easily recognize a status of the puncture. The position where the first marker 362 is provided is not limited to the distal side from the sparse pitch portion 231 of the deformation portion 230. The second marker 371 is a scale disposed on the surface of the proximal portion of the shaft portion 370 at a regular interval. Since the second marker 371 is provided, on the operator's hand side, the operator can visibly recognize the movement distance of the guide wire 360 with respect to the dilator 40 or the inserter 60. Therefore, the operator can recognize the pushing distance of the puncture portion 15, and can easily recognize the status of the puncture (for example, whether the puncture is completed). In addition, both the first markers 361 and 362 and the second marker 371 are provided. In this manner, while the pushing distance of the puncture portion 15 is adjusted by the second marker 371, the status of puncture can be confirmed by the first markers 361 and 362.

In addition, the puncture portion may not be hollow, and may be solid. In addition, the puncture portion may be a discontinuous member in the circumferential direction, and may have a C-shaped cross-sectional shape. The puncture portion can be easily formed by pressing a plate material, for example. The puncture portion may be fixed to the shaft portion through welding or bonding or may be integrally formed with the shaft portion.

Figure 30:
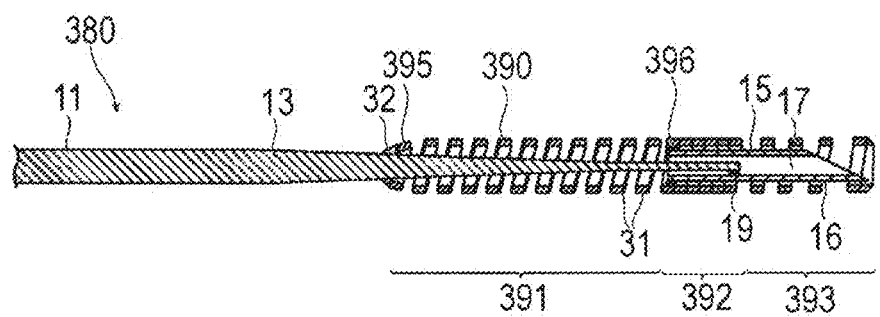
FIG. 30 is a sectional view illustrating a guide wire according to a twenty-first modification example.

In addition, as in a twenty-first modification example illustrated in FIG. 30, a deformation portion 390 of a guide wire 380 may include a proximal tapered portion 395, a first sparse pitch portion 391, a dense pitch portion 392 located on the distal side from the first sparse pitch portion 391, and a second sparse pitch portion 393 located on the distal side from the dense pitch portion 392. The same reference numerals will be given to elements having the same function as that of the above-described embodiment, and description thereof will be omitted.

The first sparse pitch portion 391 and the second sparse pitch portion 393 are formed using the spirally wound wire rods 31 having a gap therebetween while being adjacent to each other. The diameter of the proximal tapered portion 395 decreases in a tapered shape toward the proximal side from the first sparse pitch portion 391. The first sparse pitch portion 391 is located on the proximal side from the puncture portion 15. The dense pitch portion 392 has a shorter spiral inter-pitch distance than the first sparse pitch portion 391 and the second sparse pitch portion 393. The dense pitch portion 392 surrounds the proximal portion of the puncture portion 15. The dense pitch portion 392 can satisfactorily accommodate the puncture portion 15, since the gaps between the axially adjacent windings of the wire rod 31 are small. The second sparse pitch portion 393 surrounds at least a portion of the puncture portion 15. The deformation portion 390 is fixed to the shaft portion 11 by the first fixing portion 32 located in the proximal end of the proximal tapered portion 395. The deformation portion 390 is further fixed to the proximal portion of the puncture portion 15 by a second fixing portion 396 located in the proximal portion of the dense pitch portion 392.

The guide wire 380 is accommodated in the dilator 40. If the guide wire 380 moves to the distal side inside the dilator 40 and the distal end of the guide wire 380 comes into contact with the biological tissue, the force acting toward the proximal side is applied to the distal end of the deformation portion 390 located in the most distal portion of the guide wire 380. In this manner, the gaps between the axially adjacent windings of the wire rod 31 of the second sparse pitch portion 393 decreases, and the second sparse pitch portion 393 shrinks in the axial direction. In this manner, the distal portion of the deformation portion 390 moves to the proximal side, and the needle portion 16 is exposed from the deformation portion 390. The needle portion 16 exposed from the deformation portion 390 forms the hole in the biological tissue. If the distal end of the deformation portion 390 passes through the hole of the biological tissue subsequently to the needle portion 16, the second sparse pitch portion 393 stretches or lengthens in the axial direction due to the self-restorative force. In this manner, the deformation portion 390 covers the needle portion 16. The second fixing portion 396 is disposed on the distal side of the first sparse pitch portion 391. Accordingly, the first sparse pitch portion 391 does not shrink. The deformation portion 390 includes the first sparse pitch portion 391 which does not shrink, on the proximal side of the puncture portion 15. Accordingly, the fluid is easily circulated to the through-hole 17 via the wide gap of the first sparse pitch portion 391. In this manner, the contrast agent or the blood can be satisfactorily circulated via the through-hole 17.

The detailed description above describes embodiments of a guide wire, a medical device and a treatment method representing examples of the inventive guide wire, medical device, and treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire for guiding an elongated tubular body that is configured to be inserted into a living body, the guide wire comprising:
    a flexible and elongated shaft portion, the shaft portion possessing a distal portion;
    a puncture portion located at the distal portion of the shaft portion to form a hole in a first biological tissue, the puncture portion possessing a distal end;
    a deformable deformation positioned to cover the shaft portion
    the deformation portion being positionable inside the elongated tubular body and restricting deflection of the distal portion of the shaft portion;
    the shaft portion including a shaft diameter decreasing portion possessing an outer diameter that decreases in a tapering manner toward the distal portion of the shaft portion, the deformation portion being fixed to the shaft diameter decreasing portion of the shaft portion;
    the deformation portion including a wire rod that is spirally wound so that the deformation portion includes a plurality of axially adjacent windings, the axially adjacent windings in a first axially extending portion of the spirally wound wire rod being in contact with one another, the axially adjacent windings in a second axially extending portion of the spirally wound wire rod being spaced apart from one another;
    when a distal end of the deformation portion contacts the first biological tissue while the deformation portion is accommodated inside the elongated tubular body, an axial distance between at least some of the axially adjacent windings in the second axially extending portion of the spirally wound wire rod is reduced so that the deformation portion elastically shortens in an axial direction and the distal end of the puncture portion is exposed distally beyond the distal end of the deformation portion to form the hole in the first biological tissue;
    the hole in the first biological tissue being penetrable by the deformation portion after the puncture portion forms the hole in the first biological tissue, and in response to the deformation portion penetrating through the hole in the first biological tissue, the deformation portion covering the puncture portion while the deformation portion penetrates through the hole in the first biological tissue; and
    when the distal end of the deformation portion contacts a second biological tissue while the deformation portion penetrates through the hole in the first biological tissue and the deformation portion is located outside the elongated tubular body, the deformation portion is deflected together with the distal portion of the shaft portion while the deformation portion covers the puncture portion.

2. The guide wire according to claim 1, wherein the deformation portion restricts the deflection of the distal portion of the shaft portion when the deformation portion contacts the first biological tissue while the deformation portion is accommodated inside the elongated tubular body.

3. The guide wire according to claim 1, wherein the deformation portion is a tubular member possessing an interior configured to receive and cover the puncture portion.

4. The guide wire according to claim 1, wherein the deformation portion is located at an outer periphery of at least the shaft diameter decreasing portion of the shaft portion so that the deformation portion encircles the outer periphery of at least the shaft diameter decreasing portion of the shaft portion.

5. The guide wire according to claim 1, wherein a proximal end of the deformation portion is fixed to the shaft diameter decreasing portion of the shaft portion.

6. The guide wire according to claim 1, wherein the outer diameter of the shaft diameter decreasing portion decreases in a tapering manner toward the distal portion of the shaft portion, and the proximal end of the deformation portion is fixed to the shaft diameter decreasing portion of the shaft portion.

7. A guide wire for guiding an elongated tubular body that is configured to be inserted into a living body, the guide wire comprising:
    a flexible and elongated shaft portion, the shaft portion possessing a distal portion;
    a puncture portion located at the distal portion of the shaft portion to form a hole in a first biological tissue;

a deformable deformation portion positioned in covering relation to the puncture portion, the deformation portion possessing a distal end;

the shaft portion including a shaft diameter decreasing portion possessing an outer diameter that decreases toward the distal portion of the shaft portion, the deformation portion being fixed to the shaft diameter decreasing portion of the shaft portion;

the deformation portion including a plurality of axially adjacent windings in a first axially extending portion that are in contact with one another and a plurality of axially adjacent windings in a second axially extending portion that are spaced apart from one another;

when a distal end of the deformation portion contacts the first biological tissue while the deformation portion is accommodated inside the elongated tubular body, at least some of the axially adjacent windings in the second axially extending portion approach one another so that the deformation portion elastically shortens in an axial direction and the distal end of the puncture portion is exposed distally beyond the distal end of the deformation portion to form the hole in the first biological tissue;

the hole in the first biological tissue being penetrable by the deformation portion after the puncture portion forms the hole in the first biological tissue, and the deformation portion covering the puncture portion after the deformation portion penetrates through the hole in the first biological tissue and is located outside the elongated tubular body; and when the deformation portion advances and the distal end of the deformation portion contacts a second biological tissue while the deformation portion penetrates through the hole in the first biological tissue and the deformation portion is located outside the elongated tubular body, the deformation portion is deflected together with the distal portion of the shaft portion while the deformation portion covers the puncture portion.

8. The guide wire according to claim 7, wherein the deformation portion comprises a wire rod that is spirally wound to define the plurality of axially adjacent windings in the first axially extending portion and the plurality of axially adjacent windings in the second axially extending portion.

9. The guide wire according to claim 8, wherein a distal-most end portion of the elongated shaft portion axially overlaps at least some of the axially adjacent windings in the second axially extending portion.

10. The guide wire according to claim 7, wherein the puncture portion includes a distal-most end at which is located a sharp needle portion to puncture the first biological tissue, the sharp needle portion being covered by a portion of the axially adjacent windings in the second axially extending portion.

11. The guide wire according to claim 7, wherein a proximal end of the deformation portion is fixed to the shaft diameter decreasing portion of the shaft portion.

12. The guide wire according to claim 11, wherein
the outer diameter of the shaft diameter decreasing portion decreases in a tapering manner toward the distal portion of the shaft portion, and
the proximal end of the deformation portion is fixed to the shaft diameter decreasing portion of the shaft portion.

13. A guide wire for guiding an elongated tubular body that is configured to be inserted into a living body, the guide wire comprising:
a flexible and elongated shaft portion, the shaft portion possessing a distal portion;

the shaft portion including a shaft diameter decreasing portion possessing an outer diameter that decreases toward the distal portion of the shaft portion;

a puncture portion located at the distal portion of the shaft portion and configured to puncture a first biological tissue and form a hole in the first biological tissue, the puncture portion possessing a distal end;

an axially expandable and contractable cover portion fixed to the shaft diameter decreasing portion of the shaft portion and covering a distal end of the puncture portion;

the cover portion including a first plurality of windings that are in contact with one another and a second plurality of windings that are spaced apart from one another in an axial direction;

when a distal end of the cover portion contacts the first biological tissue while the cover portion is accommodated inside the elongated tubular body, at least some of the second plurality of windings approach one another in the axial direction so that the cover portion elastically shortens in the axial direction and the distal end of the puncture portion is exposed distally beyond the distal end of the cover portion to form the hole in the first biological tissue;

the hole in the first biological tissue being penetrable by the cover portion after the puncture portion forms the hole in the first biological tissue, and in response to the cover portion penetrating through the hole in the first biological tissue, the cover portion covering the puncture portion while the cover portion penetrates through the hole in the first biological tissue and the cover portion is located outside the elongated tubular body; and when the cover portion advances and the distal end of the cover portion contacts second biological tissue while the cover portion penetrates through the hole in the first biological tissue and the cover portion is located outside the elongated tubular body, the cover portion being deflected together with the distal portion of the shaft portion, and the cover portion continuing to cover the puncture portion after puncturing the first biological tissue.

14. The guide wire according to claim 13, wherein the puncture portion includes a distal-most end at which is located a sharp needle portion to puncture the first biological tissue, the sharp needle portion being covered by some of the second plurality of windings before puncturing the first biological tissue.

15. The guide wire according to claim 13, wherein the puncture portion is hollow throughout a length of the puncture portion and includes a distal-most end at which is located a sharp needle portion to puncture the first biological tissue, the puncture portion being fixed to the cover portion and being fixed to the flexible and elongated shaft portion.

16. The guide wire according to claim 13, wherein the puncture portion is hollow throughout a length of the puncture portion and includes a distal-most end at which is located a sharp needle portion to puncture the first biological tissue, the cover portion including a wire rod that is spirally wound to define the first plurality of windings and the second plurality of windings.

17. The guide wire according to claim 13, wherein a proximal end of the cover portion is fixed to the shaft diameter decreasing portion of the shaft portion.

18. The guide wire according to claim 17, wherein
the outer diameter of the shaft diameter decreasing portion decreases in a tapering manner toward the distal portion of the shaft portion, and
the proximal end of the cover portion is fixed to the shaft diameter decreasing portion of the shaft portion.

* * * * *